US007445938B2

(12) United States Patent
Angeley

(10) Patent No.: US 7,445,938 B2
(45) Date of Patent: Nov. 4, 2008

(54) SYSTEM AND METHOD FOR DETECTING PRESENCE OF ANALYTES USING GRATINGS

(75) Inventor: David G. Angeley, Charlottesville, VA (US)

(73) Assignee: General Dynamics Advanced Information Systems, Inc., Fairfax, VA (US)

( * ) Notice: Subject to any disclaimer, the term of this patent is extended or adjusted under 35 U.S.C. 154(b) by 283 days.

(21) Appl. No.: 10/990,540

(22) Filed: Nov. 18, 2004

(65) Prior Publication Data
US 2005/0068543 A1    Mar. 31, 2005

Related U.S. Application Data

(63) Continuation-in-part of application No. 10/350,508, filed on Jan. 24, 2003, now Pat. No. 7,027,163.

(51) Int. Cl.
*G01N 21/00* (2006.01)
(52) U.S. Cl. .................. 436/164; 356/244; 356/246; 356/436; 356/440; 356/521; 422/82.05; 422/82.11; 435/287.2; 435/288.7; 436/165; 436/524; 436/527; 436/805
(58) Field of Classification Search ............. 422/82.05, 422/82.11; 435/287.2, 288.7; 436/164, 165, 436/524, 527, 805; 356/521, 244, 246, 436, 356/440
See application file for complete search history.

(56) References Cited

U.S. PATENT DOCUMENTS

| 4,487,839 | A | 12/1984 | Kamentsky |
| 4,517,456 | A | 5/1985 | Halsall et al. |
| 4,876,208 | A | 10/1989 | Gustafson et al. |
| RE33,581 | E | 4/1991 | Nicoli et al. |
| 5,071,248 | A | 12/1991 | Tiefenthaler et al. |
| 5,081,012 | A | 1/1992 | Flanagan et al. |
| 5,082,629 | A | 1/1992 | Burgess, Jr. et al. |
| 5,196,350 | A | 3/1993 | Backman et al. |
| 5,413,939 | A | 5/1995 | Gustafson et al. |
| 5,442,169 | A | 8/1995 | Kunz |
| 5,559,601 | A | 9/1996 | Gallatin et al. |
| 5,577,137 | A | 11/1996 | Groger et al. |
| 5,578,833 | A | 11/1996 | Ohmi et al. |
| 5,679,579 | A | 10/1997 | Gustafson |

(Continued)

*Primary Examiner*—Christopher L Chin
(74) *Attorney, Agent, or Firm*—Steptoe & Johnson

(57) ABSTRACT

The present invention is directed to an optical grating sensor configured to detect a phase change in light passing though the system due to a binding event caused by an analyte. The grating sensor may include a light source that may be, for example, a coherent light source. The invention may also include a first diffraction grating having a first period. A micro-electrical mechanical system (MEMS) may be displaced from the first diffraction grating and may be configured to modulate the light received form the coherent light source. An analyte recognition material may be disposed on the surface of the first grating. A detector may be configured to receive light form the coherent light source after the light has been diffracted from the first diffraction grating and modulated by the MEMS. In another embodiment of the present invention, the grating sensor may be configured to operate in two modes. The first mode may be a mode the detect a phase change in the light due to a binding event. The second mode may include the detection of fluorescence due to a binding event and may employ tagging of the analytes.

15 Claims, 18 Drawing Sheets

U.S. PATENT DOCUMENTS

| | | |
|---|---|---|
| 5,846,843 A | 12/1998 | Simon |
| 5,922,550 A | 7/1999 | Everhart et al. |
| 5,959,292 A | 9/1999 | Duveneck et al. |
| 5,999,319 A | 12/1999 | Castracane |
| 6,060,256 A | 5/2000 | Everhart et al. |
| 6,061,166 A | 5/2000 | Furlani et al. |
| 6,180,288 B1 | 1/2001 | Everhart et al. |
| 6,221,579 B1 | 4/2001 | Everhart et al. |
| 6,312,961 B1 | 11/2001 | Voirin et al. |
| 6,326,144 B1 | 12/2001 | Bawendi et al. |
| 6,333,507 B1 | 12/2001 | Lai et al. |
| 6,573,040 B2 | 6/2003 | Everhart et al. |
| 6,579,673 B2 | 6/2003 | McGrath et al. |

…

SYSTEM AND METHOD FOR DETECTING PRESENCE OF ANALYTES USING GRATINGS

CROSS REFERENCE TO RELATED APPLICATIONS

This application is a continuation-in-part of U.S. patent application Ser. No. 10/350,508, filed on Jan. 24, 2003 now U.S. Pat. No. 7,027,163, entitled "Grating Sensor", which is hereby incorporated by reference in its entirety.

FIELD OF THE INVENTION

The invention relates to sensor devices for detecting the presence of an analyte. More particularly, the present invention relates to sensor devices for detecting the presence of a chemical or biological agent. More specifically, the present invention relates to chemical and biological agent sensor devices that detect phase changes in diffracted light when the light is incident on at least two diffraction grating sections.

BACKGROUND OF THE INVENTION

Biological and chemical weapons, infectious diseases, and environmental pathogens threaten both military and civilian personnel. Current technology lacks the capability to accurately detect the presence of trace amounts of, for example, chemical and biological warfare agents quickly and reliably. The present invention seeks to improve on the sensitivity, speed and/or the reliability of such prior art sensors.

Current technologies include those involving detection of analytes labeled with a fluorescent, photo-luminescent, radioactive or enzymatic marker. For example, the technique of radioimmunoassay may measure the competition between radioactively labeled analyte and unlabeled analyte for binding sites on an antibody in an antiserum. Several deficiencies in radioimmunoassay methodology have been identified. First of all, it is necessary to make a physical separation of the antibody-bound, radiolabeled analyte from the free radiolabeled analyte. Furthermore, the methodology is very time-intensive and requires substantial labor to employ.

Another broad category of currently used sensors includes those that employ optical waveguides. Waveguide sensors typically have disadvantages of high sensitivity to changes in the ambient conditions such as temperature, resulting in undesirable signal to noise ratios.

Other traditional sensors may be configured to monitor the changes in the irradiance of several diffraction orders to detect the occurrence of a biological binding event. However, irradiance measurements are not sensitive enough for many applications and are sensitive to noise, resulting in difficulty in relating and quantifying the changes in the detected diffraction irradiance signal to an input stimulus.

Some exemplary issues involved with detection architectures may include sensitivity issues (e.g., a low limit of detection) with a high probability of detection (i.e., low false negatives); a low probability of false positives; and a rapid response time or various combinations of these issues.

In summary, some exemplary problems with traditional sensors may include complexity of the system needed to evaluate for the presence of an analyte; the intensive training required to operate such complex systems; relatively time-consuming detection processes to identify the presence of an analyte; and resolution of the sensor, or the ability to detect very small amounts of analyte.

SUMMARY OF THE INVENTION

Thus, the present invention seeks to address at least some of the foregoing problems identified in prior art sensors, particularly those that detect chemical and biological agents. Thus, the present invention pertains to a system and method for detecting, for example, trace amounts of analyte using a grating-based sensor. The sensor may be configured for use with an illumination source and a signal detector in an exemplary embodiment of the system. This system may include, for example, a first and second periodic grating that is superimposed and shifted laterally relative to each other by a distance of less than one period, for example. This embodiment may permit the illumination from the source to be affected by both gratings prior to reaching the detector. An analyte recognition material may be disposed on a surface of, for example, the second diffraction grating. Alternative embodiments of the present invention may include the use of a MEMS device to modulate the signal received from a grating having an analyte recognition material deposited upon the grating.

The invention according to a first aspect may include a first periodic diffraction grating and a second periodic diffraction grating. The gratings may be superimposed on one another and may also be shifted relative to one another by a distance of less than one grating period. An analyte recognition material may be disposed on the surface of one of the diffraction gratings, such as, for example, the second diffraction grating. A sensor according to this first aspect of the present invention may also include an analyte recognition material. The analyte recognition material may be disposed on a surface of the second diffraction grating. The sensor according to the first aspect of the present invention may also include an illumination source directing illumination onto the first grating. A detector may be disposed relative to the second grating such that illumination passing through the second diffraction grating is incident upon the detector.

According to another aspect of the invention, the optical sensor may include a positioning system. In one embodiment of the invention, the positioning system may be configured to move one or both of the first and second gratings. According to yet another aspect of the present invention, the optical sensor may also include a spatial filter. The spatial filter may be disposed such that predetermined orders of diffracted light are prevented from reaching the detector. According to another aspect of the present invention, the distance of less than one period may be, for example, ¼ period. Various analyte recognition materials may also be used in connection with the present invention. Such analyte recognition materials include, for example, antibodies, nucleic acids, or lectins.

According to another embodiment of the present invention, the invention may include a method of detecting an analyte. The method may include the steps of providing an optical sensor. Once the optical sensor has been provided, the output of the detector within the optical sensor may be sampled to establish a baseline optical phase signal. After the baseline signal has been established, the analyte recognition material may be exposed to an analyte. The analyte may be a biological sample. By way of example, the sample may be obtained from a mammal. The mammal may be, for example, a human. Alternatively, the sample may come from, for example, the environment. After the analyte recognition material has been exposed to the sample the output of the detector may be sampled to determine a second optical phase signal. After the second optical phase signal has been obtained, the baseline optical phase signal may be compared to the second optical phase signal to detect the presence of the analyte, if any, within the sample by identifying a shift in phase of the signal.

According to another aspect of the invention, the optical sensor may include a positioning system for moving one or both of the first and second gratings. Additionally, or in the alternative, the optical sensor may also include a spatial filter disposed relative to the second grating such that predetermined orders of diffracted light are prevented from reaching the detector. According to another aspect of the present invention, the distance of less than one period may be, for example, ¼ period. Various analyte recognition materials may also be used. Such analyte recognition materials include, for example, antibodies, nucleic acids, or lectins. According to another embodiment of the present invention, the step of comparing the first and second optical phase measurements may be performed to determine an amount (i.e., the concentration) of the analyte in the sample.

According to a third aspect of the present invention, an optical sensor configured for use with an illumination source and a signal detector may include a first periodic grating and a second periodic grating. The gratings may be superimposed and shifted laterally with respect to the grating surface normals relative to each other by a distance of less than one period such that the illumination from the source is affected by both gratings before reaching the detector. Furthermore, the second diffraction grating may include an analyte recognition material disposed thereon. The invention according to a third aspect may also include a positioning system. The positioning system may be configured to move one or both of the first and second gratings. Additionally, or in the alternative, the optical sensor may also include a spatial filter disposed relative to the second grating such that predetermined orders of diffracted light are prevented from reaching the detector. According to another aspect of the present invention, the distance of less than one period may be, for example, ¼ period. Various analyte recognition materials may also be used. Such analyte recognition materials include, for example, antibodies, antigen, peptides, nucleic acids, cells, phage displays, proteins, lectins, molecular imprinted polymers (MIPs), fullerenes, carbon nanotubes, or general carbon nano-systems.

The invention according to a fourth aspect may include a light source. The light source may be, for example, a coherent light source. The invention may also include a first diffraction grating having a first period. A micro-electrical mechanical system (MEMS) may be displaced from the first diffraction grating and may be configured to modulate the light received from the coherent light source. An analyte recognition material may be disposed on the surface of the first grating. A detector may be configured to receive light from the coherent light source after the light has been diffracted from the first diffraction grating and modulated by the MEMS.

The invention according to a fourth aspect may also include a spatial filter disposed relative to the MEMS such that predetermined orders of diffracted light are prevented from reaching the detector. According to one embodiment of the present invention, the MEMS may be configured to modulate the light at a frequency of approximately 1 kHz or more. Alternatively, the MEMS may be configured to modulate the light at a frequency of 10 kHz or more. An analyte recognition material configured to be used in connection with the fourth aspect of the present invention may be, for example, an antibody, a nucleic acid, or a lectin. In yet another embodiment of an invention according to a fourth aspect of the present invention, the detector may be one of two detectors. According to this embodiment of the invention, the apparatus may include a fluorescent light source that is configured to excite a fluorescent marker thereby causing spontaneous emission from the fluorescent marker. Additionally, the apparatus may also include a second detector configured to receive energy from the spontaneous emission.

A method according to a fifth aspect of the present invention may include a step of illuminating a first grating with light from a coherent light source. This first grating may have an analyte recognition material disposed on the surface of the grating. Additionally, the method may include receiving the light from the coherent light source at a micro-electrical mechanical system (MEMS) after light passes through the grating including the analyte recognition material. The light received at the MEMS may then be modulated at a frequency. According to one embodiment of the invention, the light may be modulated at 1 kHz. Alternatively, the light may be modulated at 10 kHz. The phase of the light may be detected after it is modulated by the MEMS using a detector.

The MEMS may be configured to simulate a lateral displacement of a grating with respect to the first grating in a manner analogous to the first, second and third aspects of the present invention. The lateral displacement may be, for example, less than one period. According to one preferred embodiment of the present invention, the displacement may be, for example, ¼ period. The step of detecting a phase of the light received from the MEMS at a detector may include detecting a phase change of the light due to a binding event at the analyte recognition material disposed on the first grating.

The invention according to a sixth aspect may include a grating-based optical sensor. The grating-based optical sensor may be configured to operate in two modes. The first mode may be configured to detect the presence of an analyte based on a binding event. The binding event may result in an associated phase change of the light as it passes through, for example, a first grating. This phase change may be caused by the binding of an analyte to the analyte recognition material resulting in a change of the grating height. The second mode may be configured to detect the presence of the analyte using tagging of the analyte. The tagging may be, for example, a fluorescence tagging. In one embodiment of the invention, the first mode may employ the use of a micro-electro mechanical system (MEMS) to modulate the light received from a first grating. The first grating may have an analyte recognition material disposed thereon. The grating-based optical system may be configured to operate in the first mode and the second mode concurrently. Alternatively, the grating-based optical sensor may be configured to operate selectively in the first mode and the second mode.

BRIEF DESCRIPTION OF THE DRAWINGS

While the specification concludes with claims particularly pointing out and distinctly claiming the present invention, it is believed the same will be better understood from the following description taken in conjunction with the accompanying drawings, which illustrate, in a non-limiting fashion, the best mode presently contemplated for carrying out the present invention, and in which like reference numerals designate like parts throughout the Figures, wherein:

DETAILED DESCRIPTION OF THE INVENTION

The present disclosure will now be described more fully with reference the to the Figures in which various embodiments of the present invention are shown. The subject matter of this disclosure may, however, be embodied in many different forms and should not be construed as being limited to the embodiments set forth herein.

A grating sensor according to the present invention may be, for example, a photonic device that includes an optical grating structure having at least two individual gratings. According to one embodiment of the present invention, the two gratings, each having a periodic structures, may be positioned parallel to each other, such that the periodic structure are superimposed and shifted laterally with respect to a normal to the grating surface relative to each other. According to this embodiment of the invention, the lateral shift may be less than one period. According to a preferred embodiment of the present invention, the lateral shift may be a shift of one-quarter period. Furthermore, at least one of the gratings may include an analyte recognition material disposed on the grating surface and operable to interact specifically with an analyte of interest. A change in the optical depth of modulation in one of the gratings may be caused by a specific interaction of an analyte with the analyte recognition material may result in a change in optical phase of the photonic energy (e.g., associated with the electric field vector associated with a photonic wave) passing though the first grating. This phase change may be sensed by a detector and may be output as an electrical signal. The grating sensor according to this embodiment may include a translation device adapted to move one or more of the gratings in order to modulate the signal.

Figure 1:
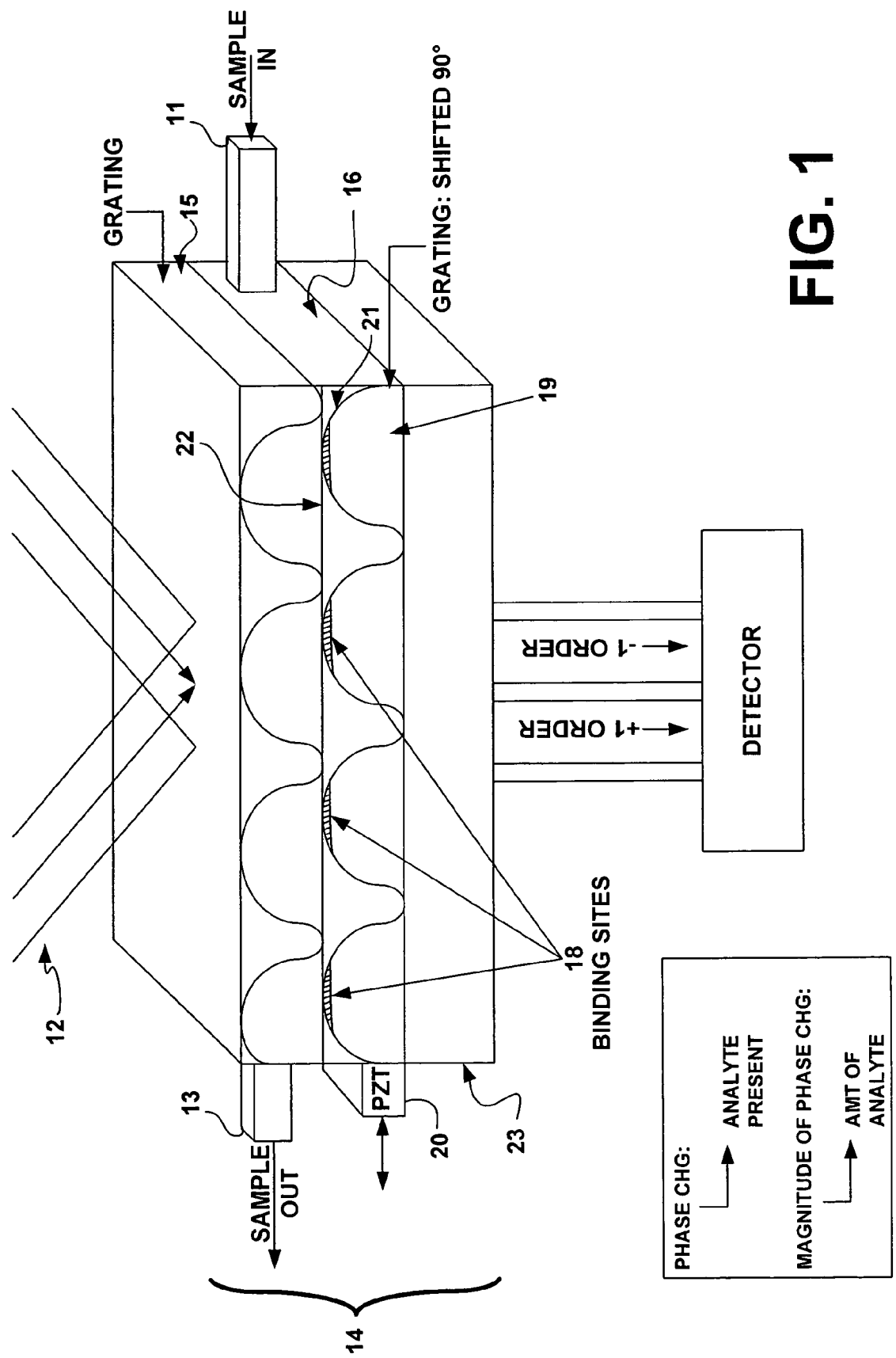
FIG. 1 shows an embodiment of a grating sensor according to one embodiment of the present invention.

FIG. 1 shows an embodiment of a grating sensor 10 according to one embodiment of the present invention. Incident light 12 may be scattered or diffracted into diffractive orders by, for example, the grating structure 14. In this embodiment of the invention shown in FIG. 1, the grating structure may include, for example, two periodic diffractive gratings 15, 16. The properties of the diffracted or scattered light may be based on the various features of the grating structure 14, including, for example, the period of the grating and the grating height. A physical change in the grating structure 14, caused, for example, by the interaction of an analyte 18 with the analyte recognition material 19, which may be disposed on the grating structure 14, causes a change in the phase of the light, which is sensed by a detector 17. The detector 17 may be configured to quantify a change in the phase of the light. A positioning system 20 is also shown in FIG. 1. The positioning system 20 may be configured to modulate the output signal by moving one or more of the gratings relative to the other.

Figure 2:
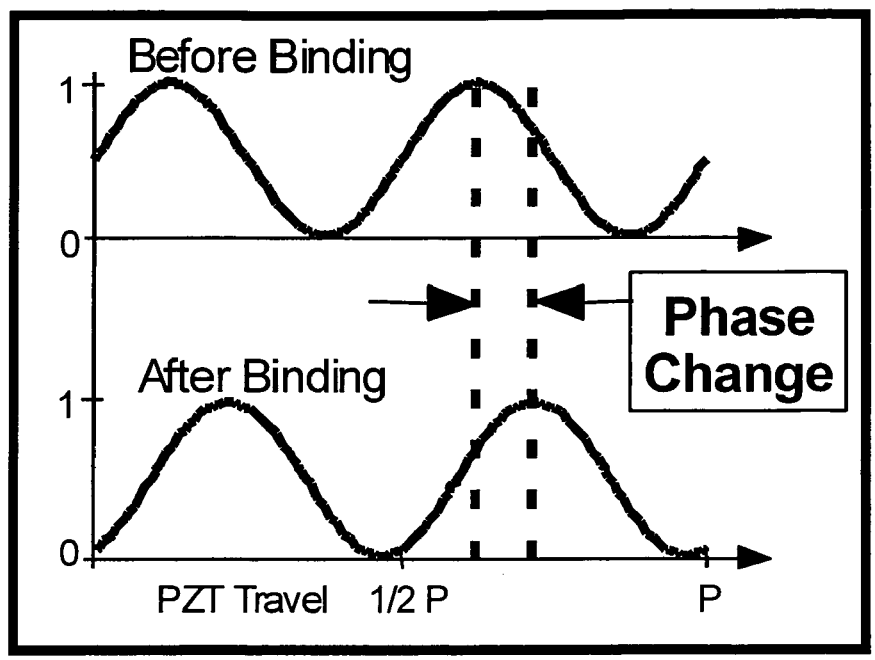
FIG. 2 shows an exemplary normalized output intensity profile from a grating sensor according to an embodiment of the present invention.

FIG. 2 shows an exemplary normalized output intensity profile from a grating sensor according to an embodiment of the present invention. As FIG. 2 shows, after a binding event occurs, the phase of the light transmitted through the grating structure 14 is changed.

Gratings that are suitable for use in a sensor according to various aspects of the present invention and methods of making such gratings will now be described. A grating may be selected for a particular sensor application according to the characteristics and properties required for the particular application. These various requirements will be understood by one of ordinary skill in the art. Characteristics and modifiable properties of individual gratings are set forth in references such as Hutley M. et al., *Diffraction Gratings*, Academic Press (1997) and E. Popov, et al., *Diffraction Gratings and Applications*, Marcel Dekker, Inc. (1997), each of which are hereby incorporated by reference in their entirety. Modifiable grating parameters include, for example, grating period, index of refraction, and modulation depth. The period of the grating may determine the angle of the diffractive orders. Additionally, the peak-to-valley excursion of the phase or optical path (i.e., refractive index profile) determines the amount of light that is diffracted into each order. The lateral position with respect to the normal to the grating surface of the grating may determine the phase of the wavefront in each of the diffractive orders relative to the zero order. Further modifiable grating parameters include material composition of the grating, grating surface chemistry and type of analyte recognition material used, as described in more detail below. An illustrative grating suitable for use in a sensor according to the present invention is described in Example 1 below.

Such a grating suitable for use in a sensor employing the present invention may include a substrate material. The substrate material may be a solid. According to another embodiment of the present invention, the substrate material may be a firm gel. Some exemplary materials may include, for example, glass, silicon, metals such as aluminum, copper, gold, platinum, titanium or alloys thereof, graphite, mica, and various polymers, such as polystyrene; polycarbonate, polymethylmethacrylate; polyvinylethylene; polyethyleneimine; polyoxymethylene; polyvinylphenol; polyactides; polymethacrylimide; polyalkenesulfone; polyhydroxyethylmethacrylate; polyvinylidenedifluoride; polydimethylsiloxane; polytetrafluorethylene; polyacrylamide; polyimide and block-copolymers. Choice of grating material may depend on a number of factors such as, for example, the analyte sought to be detected, the analyte recognition material to be used and the surface chemistry suitable for immobilizing the analyte recognition material on the grating.

The substrate material of the grating used in a sensor according to the various embodiments of the present invention may include a modified surface for immobilizing an analyte recognition material by chemical bonding or adsorption. Surface modification, by for example, chemical treatment of a surface to provide binding sites for an analyte recognition material may depend on the particular analyte recognition material to be attached to the substrate and the composition of the substrate. Modification of grating surface chemistry in order to attach an analyte recognition material may include such illustrative methods as modification of silicon or silicon oxide surfaces with organo-functionalized silanes, such as alkoxy- and chloro-silanes. Further suitable silanes are listed in Silicon Compounds: Register & Review, from United Chemical Technologies, 5th Ed., 1991. In addition, many other surface chemistries and methods of modifying a grating substrate for binding an analyte recognition material are known, such as those commonly used to fabricate microarrays of proteins, nucleic acids, and other materials. See, e.g., M. Schena, et al., "Quantitative Monitoring of Gene Expression Patterns with a Complementary DNA Microarray", Science, 270: 467-70, 1995; Hermanson et al., Immobilized Affinity Ligand Techniques, Academic Press, Inc., 1992 and U.S. Pat. Nos. 6,479,301, 6,475,809, 6,444,318 and 6,410,229, each of which are hereby incorporated by reference in their entirety.

Advantageously, attachment of an analyte recognition material may be reversible such that the sensing surface of the grating is reusable.

An analyte recognition material may be included on at least one of the gratings used in a sensor of the invention. As used herein, the term "analyte recognition material" is intended to mean an atomic or molecular structure that specifically binds to an entity to be detected, i.e., an analyte.

Analytes detected by a grating sensor according to the invention may include, for example, an antibody, an antigen, a hapten, a receptor, a receptor ligand such as an agonist or antagonist, a lectin, a protein, a peptide, a polysaccharide, a toxin, a virus, a bacterium, a cell, a cell component such as an organelle, a particular such as a liposome or noisome, a nucleic acid, a drug and a prion. An analyte material may be a fragment or metabolite of the substances listed above capable of specific interaction with an analyte recognition material. Nucleic acids may include, for example, DNA, RNA, oligomers and aptamers. An analyte may also be a gas, such as, for example, NO, $O_2$, and $CO_2$.

Exemplary analyte recognition materials immobilized on a grating may include, for example, an antigen, antibody, hapten, carbohydrate, lectin, receptor, ligand, binding protein, toxin, substrate, enzyme, peptide, cell, phage display, molecular imprinted polymer (MIP), fellerene, carbon nanotube, and nucleic acid.

Specific interactions between an analyte and an analyte recognition material are well known in the art, as are reaction conditions under which specific interactions occur. Interactions between an analyte recognition material may include, for example, antigen-antibody, carbohydrate-lectin, receptor-ligand, binding protein-toxin, substrate-enzyme, effector-enzyme, inhibitor-enzyme, nucleic acid pairing, binding protein-vitamin, binding protein-nucleic acid, reactive dye-protein, and reactive dye-nucleic acid. Reaction conditions including, for example, variables such as temperature, salt concentration, pH, diffusion rates, flow geometry, and reaction time are known to affect binding and one of skill in the art will recognize the appropriate binding conditions for a particular analyte/analyte recognition material pair. Specific conditions are set forth in common references such as, for example, Bowtell et al., DNA Microarrays: A Molecular Cloning Manual, Cold Spring Harbor Laboratory, 2002; Sambrook et al., Molecular Cloning: A Laboratory Manual, Cold Spring Harbor Laboratory; $3^{rd}$ edition, 2001; and Harlow et al., Using Antibodies: A Laboratory Manual: Portable Protocol No. 1, Cold Spring Harbor Laboratory, 1998, each of which are hereby incorporated by reference in their entirety.

Creating structured arrays of analyte recognition materials may require the immobilization of those materials at discrete locations on the surface of the grating. Exemplary techniques used include photoresist technology, self-assembled monolayer deposition and photochemical techniques. Deposition and patterning of an analyte recognition material contribute to a modification of the refractive index of a particular grating. Adjustment of the refractive index profile of the grating may be one method of modulating the sensitivity of the grating sensor.

An exemplary method of analyte recognition material deposition and patterning is micr-contact printing, which is a type of soft lithography that transfers molecules onto substrates at specific locations with the use of a polymeric stamp that has been cast from a desired pattern set in a master die. This procedure is an established microfabrication technique for patterning chemicals, proteins, DNA, lipid membranes, and cells. A polymer stamp, typically a material such a poly dimethyl siloxane (PDMS), has the analyte recognition material to be patterned adsorbed to it, rinsed and dried, and then placed into contact with a solid substrate. After some predetermined time, which may range from seconds to minutes, for example, the stamp may be removed and the substrate surface may be left with a coating of the transferred analyte recognition material in the described pattern. The predetermined time may be dependent on the materials used in the process as well as other conditions, as will be recognized by the ordinarily skilled artisan.

Figure 3:
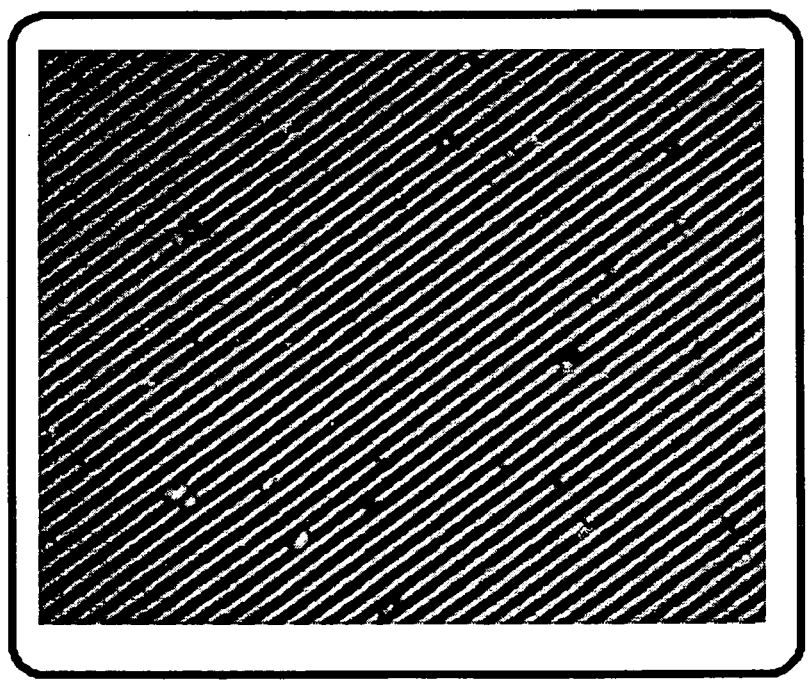
FIG. 3 shows a micrograph of an analyte recognition material deposited on a grating surface configured for use in a grating sensor according to one aspect of the present invention.

FIG. 3 shows a micrograph of an analyte recognition material deposited on a grating surface configured for use in a grating sensor according to one aspect of the present invention. More specifically, FIG. 3 shows IgG proteins patterned onto glass microscope slides using microcontact printing. A PDMS stamp is used to deposit Alexa 488 labeled rabbit anti-goat IgG on a class microscope slide. The fluorescent label was used in order to record an image using the fluorescent microscope. The data from the 4 μm period lines was recorded using a 40× magnification.

Photolithographic techniques are also well known as a method to manufacture a photoresist material in a desired pattern. A patterned photoresist may be used to mask regions of the substrate that are to be functionalized with an analyte recognition material and allow the placement of surface pacifying molecules. Once the photoresist is removed there will be rows of molecular functional groups, primed for further chemical attachment to an analyte recognition material, such as an antibody, patterned between rows of nonreactive, protein resistant surface bound species.

A further patterning method may include a photochemical method. For example, a silane monolayer may be chemisorbed onto the surface of an etched grating wafer. The silane is chosen to have a reactive functional group (e.g., thiol, amine) available for further reaction. Specific bifunctional linkers may be chosen that contain a photoactive functional group at one end. These linkers may be covalently attached to the silane film such that the photoactive group is available for further reaction/modification. The substrates may then be positioned into the optical assembly, and light from a laser source, such as, for example, a ultraviolet (UV) laser source, used to create an interference pattern on the substrate that matches the etched grating groove period. This may produce surface patterned likes of active and nonactive functional groups. The active silane functional groups may then be linked to an analyte recognition material, such as an IgG antibody. The linker molecules used in such a method may be chosen depending on the analyte recognition material to be attached and the light used in patterning. A variety of photoactive bifunctional linkers is commercially available, including bifunctional linkers that are reactive in UV light having a wavelength of about, for example, 230-350 nm.

Following surface deposition of a surface chemistry component, such as, for example, a linker or an analyte recognition material, various techniques, such as, for example, ellipsometry, and atomic force microscopy (AFM) may be used to evaluate the deposition for artifacts and/or appropriate quantity and pattern.

Although the individual grating is discussed above as incorporating a single type of analyte recognition material a grating may incorporate more than one type of analyte recognition material in order to allow multiple analyte detection on a single grating surface. According to an alternative embodiment of the invention, a grating structure may be configured to detect multiple analytes by overlaying multiple gratings in a single grating structure, much like a volume hologram, with each grating tailored to a specific analyte. In this case, differentiating between grating signals may be achieved by utilizing different grating periods or by using several wavelengths.

Prevention of nonspecific binding of analytes and/or analyte recognition materials to a grating used in an inventive sensor may be important in achieving an optimal signal to noise ratio. A number of different approaches have been used to reduce nonspecific binding to various surfaces. The adsorption of innocuous proteins such as bovine serum albumin (BSA) and casein has been used to block other proteins from binding during surface immobilization of antibodies. The attachment of poly(ethylene glycol) (PEG) groups to glass and metals has been an effective method for creating protein-resistant surfaces. An inert or innocuous peptide sequence may also be used. Detergents, in particular non-ionic types such as Tween and triton series of surfactants and zwitterionic surfactants, have been used to create "wetter" surfaces that inhibit protein surface adsorption.

The grating structure included in the grating sensor may include two gratings as described above. The individual gratings may be variably configured with respect to each other dependent on factors such as grating geometry, diffraction order selection, wavelength of the light source used and the distance between the grating surfaces. As mentioned above, the two grating surfaces, each of which may have a periodic structure, may be positioned parallel to each other, according to one embodiment of the present invention. The periodic structures may be superimposed and shifted laterally relative to one another. This lateral shift may be less than one period and may preferable a shift of ¼ period. This arrangement is shown in FIG. 1, where the individual gratings are labeled 15 and 16, as well as in FIG. 6B where the individual gratings are labeled 110 and 120.

Figure 6:
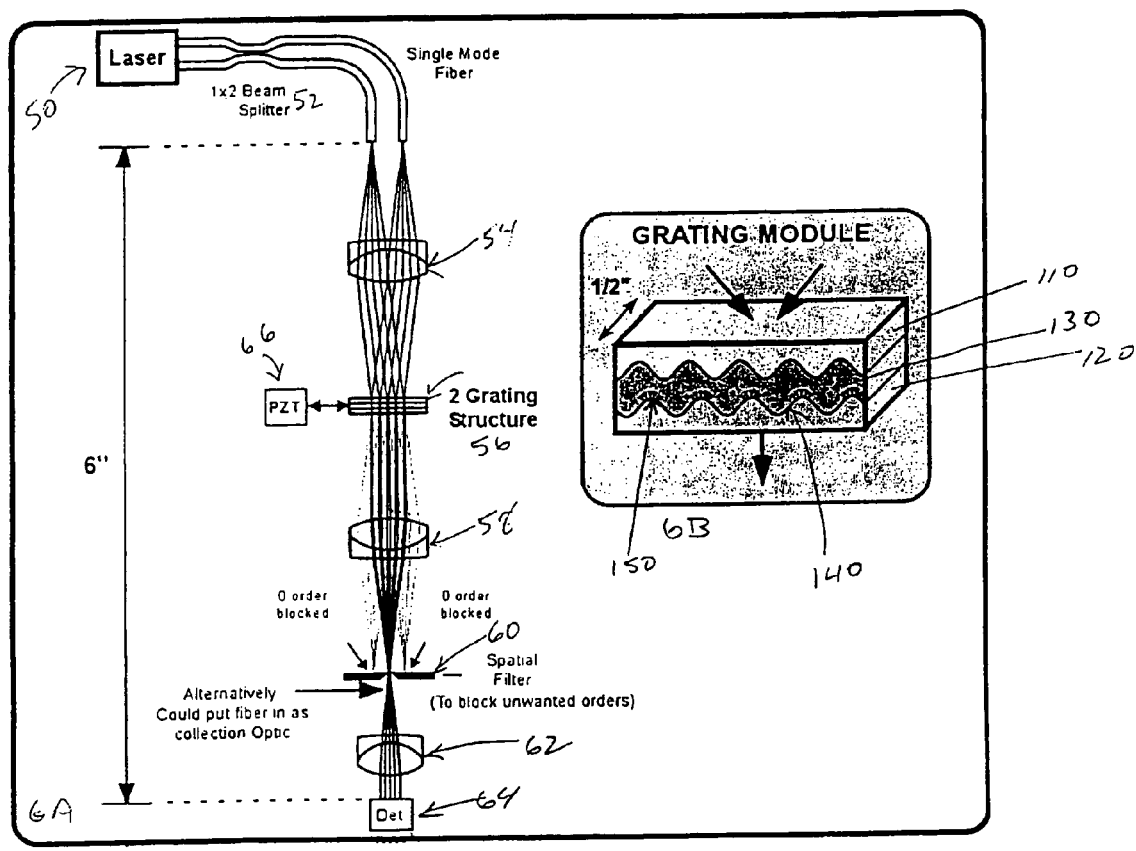
FIG. 6A shows an exemplary grating sensor according to an exemplary embodiment of the present invention.
FIG. 6B shows a grating sensor module according to an exemplary embodiment of the present invention.

In one embodiment of the present invention, as shown in FIG. 6B, a first grating 120, having a surface 140 containing an immobilized analyte recognition material 150, is disposed proximate to a second grating 110 such that a space 130 is formed between the two gratings. Materials illustratively including a buffer or a sample putatively containing an analyte to be detected may be introduced into the space 130.

In an alternative embodiment of the invention, shown in FIG. 1, a first grating 16 may include a first surface 21 containing an immobilized analyte recognition material 18 and an opposing surface 22 is disposed proximate to a second grating 15 such that the surface 21 is distal to the grating 15 and the opposite surface 22 is proximal to the grating 15. This embodiment further includes a support 23 on which grating 16 is disposed. This may create a space 19 between the grating 16 and support 23. Materials may include, for example, a buffer or a sample putatively containing an analyte to be detected may be introduced into the space 19.

In the transverse dimension, the gratings may be disposed with a minimum distance between them that allows fluid flow. This distance may be, for example, greater than one nanometer. The maximal distance between gratings may be defined by the width of the incident beam, the period of the grating, the wavelength, and the order of diffraction detected. The measurements may by relatively insensitive to the separation distance between the grating surfaces. This may be understood by the Talbot effect, the repeating self-images of the diffraction grating. These repeating self-images occur at multiples of the characteristic Talbot distances. In general, if the two gratings lie within the Rayleigh range or depth of focus of the incident beam, the maximal distance requirement is satisfied.

Figures 7A, 7B, 7C:
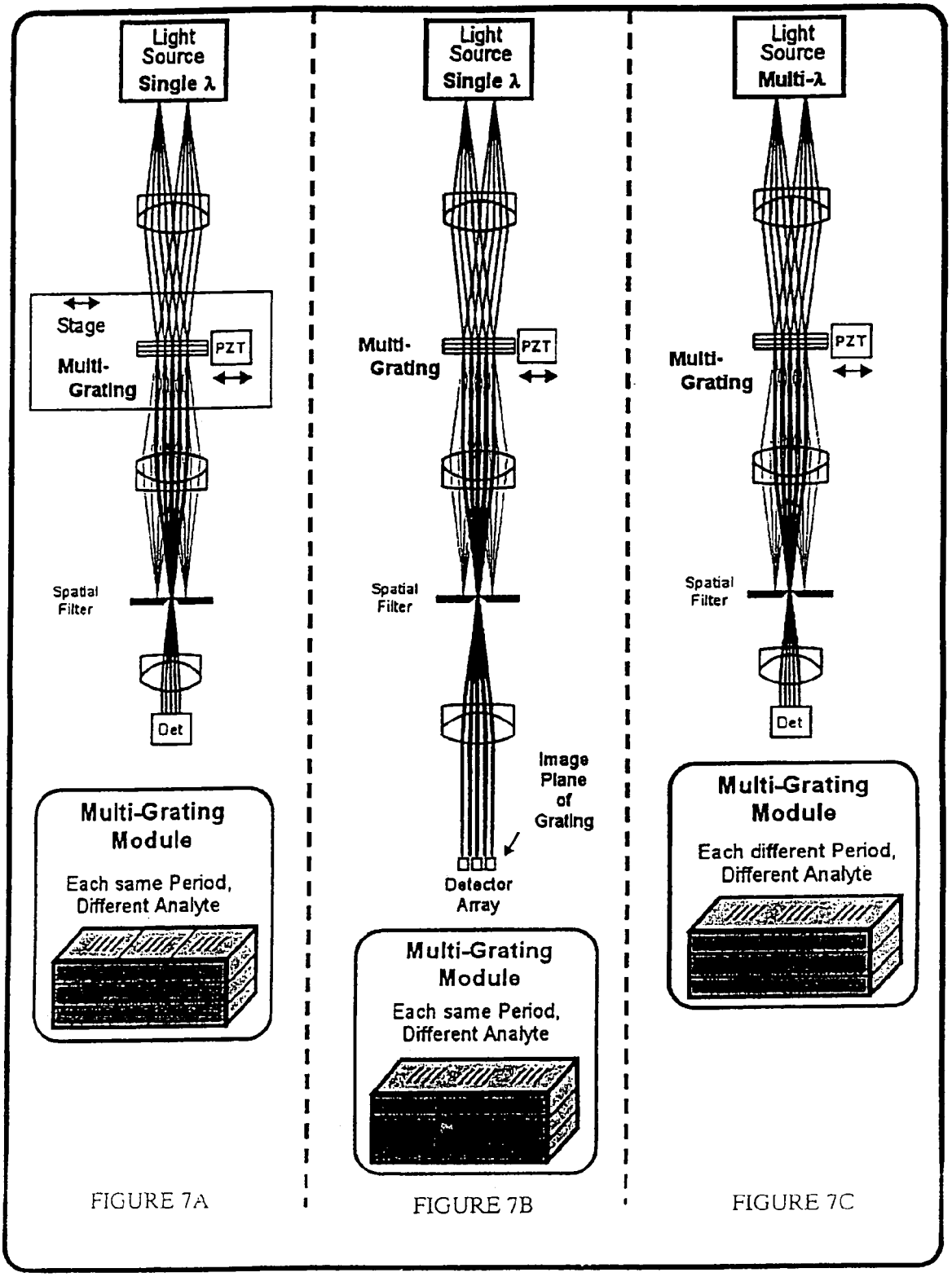
FIG. 7A shows an exemplary embodiment of a grating sensor according to one aspect of the present invention.
FIG. 7B shows another exemplary embodiment of a grating sensor according to another embodiment of the present invention.
FIG. 7C shows yet another exemplary embodiment of a grating sensor according to another embodiment of the present invention.

As discussed above, multiple analyte recognition materials and multiple gratings may be utilized to detect multiple analytes, as illustrated in FIGS. 7A, 7B and 7C, and described in Examples 3,4, and 5, below.

Any wavelength of light which is not significantly absorbed by either the grating or the solution may be used for illumination in a sensor according to the present invention. For example, a single wavelength may be used. The wavelength may be 633 nm and may be, for example, produced by a traditional He—Ne laser. In some multiple analyte detection systems according to the present invention, multiple wavelengths may be used, each detecting a separate analyte as described below and is shown in FIG. 7C.

The grating structure may be illuminated by two collimated beams, each at a specific angle, to achieve the interference between the desired orders, such as, for example, the first orders. The diffraction angle for a given period is wavelength dependent, as per the grating equation, which will be discussed in more detail below. Beam diameter is somewhat flexible. At the low end, the beam may have a diameter such that it covers at least two periods. The beam diameter may be balanced against dimensional requirements (i.e., area of the grating surface) and sufficient coverage in conjunction with the technique used to fabricate the gratings. An optimum beam diameter will take into account these factors.

A detector to be used in a sensor according to the invention is known in the art and includes such devices such as, for example, oscilloscopes, digital cameras, CCD cameras, and the like. The detection scheme may be, for example, a derivative of a lithographic overlay alignment method, currently used in lithographic projection systems, which can detect lateral shifts of semiconductor wafer features down to the 10 nm range. Such detectors are described in, for example, U.S. Pat. Nos. 5,559,601 and 5,477,057, which are hereby incorporated by reference in their entirety. A detector array may be used, for example, when multiple analytes are detected as shown in FIG. 7B.

The measurement of optical phase is a mature technology, such as is known in the field of commercial interferometry, and has inherent advantages over intensity measurements with regard to noise sources. Methods and devices for phase measurement are well known and commercially available.

A grating sensor according to the present invention may include a positioning system configured to dither the translation motion of the grating structure so as to modulate the baseline signal. Such positioning systems are known in the art and include, for example, piezo actuators such as piezoelectric transducers (PZT) that are commercially available and art recognized equivalents. According to another embodiment, a translation device with no moving parts maybe used, and may employ, for example, acoustically induced optical gratings, such as, for example, an acousto-optic grating. Modulation of the light may permit the elimination of noise sources in the detection of the optical signals received after passing through the grating sensor.

The theory of the operation of the grating sensor according to the various embodiments of the present invention will now be described. Two electromagnetic waves may be assumed. These two waves may have the following form:

$$E_1(x, y, z, t) = A_1(x, y, z)e^{i(\omega t - \phi_1(x,y,z))}$$

and $$E_2(x, y, z, t) = A_2(x, y, z)e^{i(\omega t - \phi_2(x,y,z))}$$

where A is the amplitude and $\phi$ is the phase of the wave.

The two beam interference equation for the two beams of the same polarization and optical frequency is:

$$I(x, y, z) = I_1 + I_2 + 2\sqrt{I_1 I_2}\cos(\Delta\phi(x, y, z))$$

where I is the intensity of the electric field and is equal to the modulus squared of the electric field, and $\Delta\phi$ is the phase difference ($\phi_1 - \phi_2$) between the waves.

From this equation, it can be seen that the detected intensity varies cosinusoidally with the phase difference between two waves. The alternating bright and dark bands are referred to as interference fringes.

In an exemplary grating sensor according to one embodiment of the present invention, a sinusoidal phase grating may be defined by the following transmission function:

$$T(x, y) = e^{i\frac{m}{2}\sin(2\pi fx - \psi)} rect\left(\frac{x}{l}\right) rect\left(\frac{y}{l}\right)$$

where m is the peak to peak excursion of the phase delay (optical depth modulation), f is the grating frequency), $\psi$ is the lateral shift of the grating, rect is the rectangular aperture function with a width l.

The far-field diffraction pattern when the transmission function of this equation is illuminated by a normally incident monochromatic plane wave is given by:

$$E(x_{ff}, y_{ff}) = K \sum_{q=-\infty}^{\infty} \left(J_q\left(\frac{m}{2}\right)\sinc\left(\frac{1}{\lambda z}(x_{ff} - qf\lambda z)e^{1q\psi}\right)\right)$$

where $x_{ff}$, $y_{ff}$ are the far-field transverse coordinates, q is the order of diffraction, k is a constant with all the terms not independent of the diffractive order (q) included within the constant, $J_q$ is a Bessel function of the first kind, order q, and $\lambda$ is the wavelength. From this equation it can be seen that the introduction of the phase grating has deflected energy out of the zero order into a multitude of higher order components. The intensity of these orders is dependent on $J_q(m/2)$ and phase of the orders is dependent on $\psi$, i.e., the shift, of the gratings as given by $e^{iq\psi}$.

Where the system is set up such that the +1 and the −1 orders are made to coincide so as to generate a two beam interference condition as in the equation for I(x,y,z), above, one beam would have an electric field of $E_{+1} \propto e^{i\psi}$ while the second would have $E_{-1} \propto e^{-i\psi}$. Thus, the intensity equation for the interference of the two electric fields becomes:

$$I = I_{+1} + I_{-1} + 2\sqrt{I_{+1}I_{-1}}\cos(2\psi).$$

Thus, the interference pattern is shown to be dependent on the shift of the grating. Measurement of the fringes may reflect the position of the grating. This is the basis for some of the techniques used to align wafers in lithographic processes as described, for example, in U.S. Pat. Nos. 5,559,601 and 5,477,057, which are hereby incorporated by reference in their entirety.

Measurement of the phase to yield the lateral shift of a grating may be very precise and relates to changes in the depth of modulation. Depth of modulation can be converted to a lateral shift in the position of a grating by displacing two gratings adjacent to each other with one shifted by ¼ period. Using some trigonometric relationships, it can be shown that:

$$A_1\sin(x) + A_2\cos(x) = A_3\sin(x+\psi),$$

where A is the amplitude of the sinusoidal components, and $\psi$ is the shift of the composite grating. $\psi$ is given by:

$$\psi = \arctan\left(\frac{A_2}{A_1}\right).$$

Figure 4:
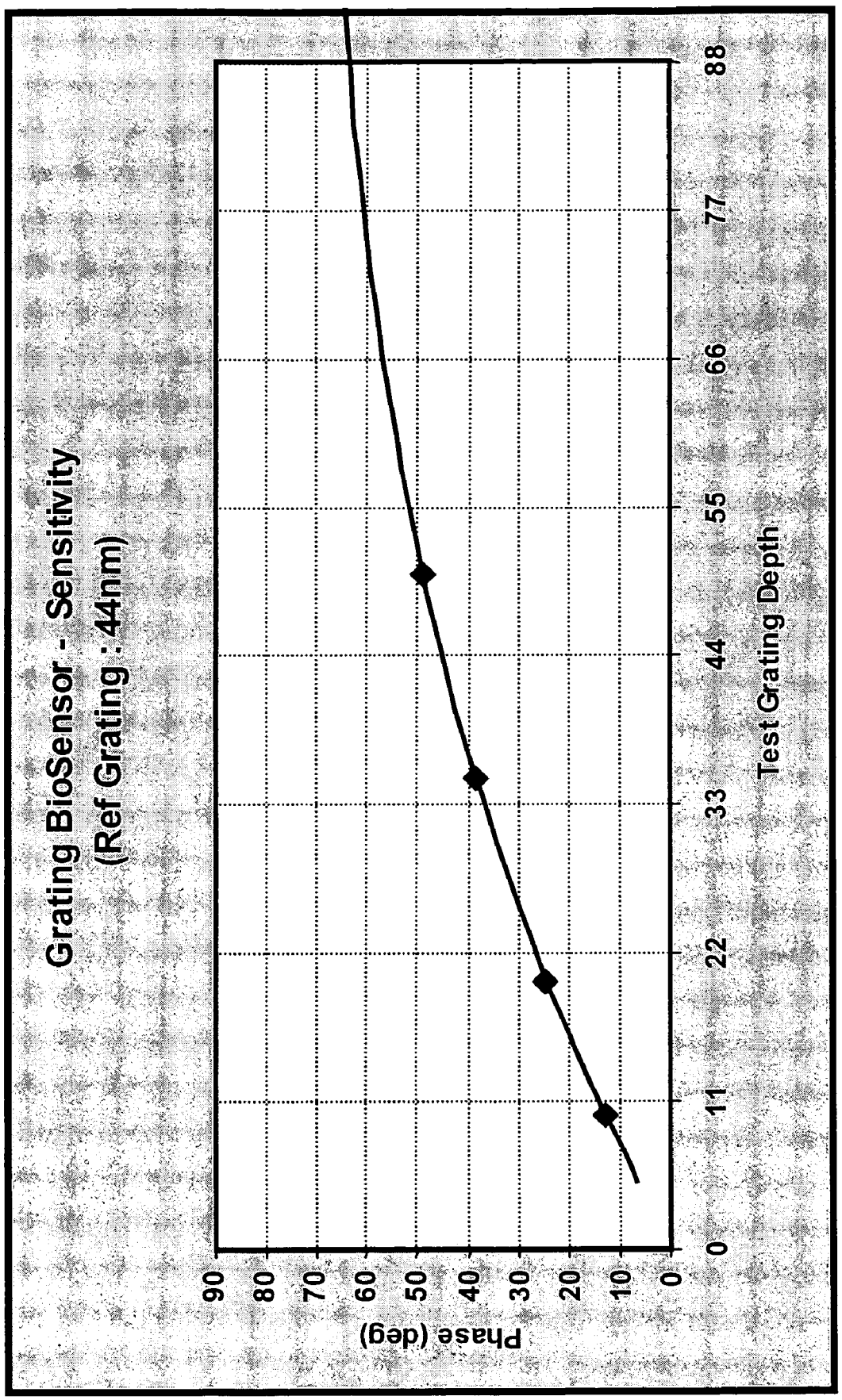
FIG. 4 shows a graph of grating shift plotted as a function of the ratio of depths of the two gratings.

Equivalently, the sinusoidal phase grating in the equation for T(x,y) may be replaced with this two grating composite. Therefore, the shift of this composite grating structure is dependent on the relative amplitudes of the two individual gratings which make it up. If $A_1$ is much larger than $A_2$, then $\psi$ approaches zero and the equation for intensity of the interference of the two electric fields is at a maximum. If $A_1$ is much larger than $A_2$, then v approaches 90 degrees and the equation for the interference of the two electric fields is at a minimum. Moving between these two conditions results in a shift in the detected intensity patterns between a minimum and a maximum, i.e., the intensity pattern shifts ½ fringe. FIG. 4 shows a graph of composite grating shift plotted as a function of the ratio of depths of the two gratings. Specifically, FIG. 4 is a graph of the equation for $\psi$ plotted against the ratio of the depths of the two gratings. In FIG. 4, one grating with a 44 nm depth is held constant and is called the reference grating. The other grating depth may vary, causing the curve illustrated in FIG. 4. Therefore, at 44 nm the ratio=1 for the grating depths. The shift is relative to the grating period. Measurement of the optical phase change between two interfering orders indicates a change in the ratio of the two grating amplitudes.

Commercial interferometry systems are available whose minimum detectable limits are $\frac{1}{1000}$ of a phase cycle. From FIG. 4, it can be seen that this technique has potential sensitivity to detect fractions of a 1 nm grating height change.

A method for using the inventive grating sensor may include a preliminarily illuminating the grating structure before exposure to the sample or analyte in order to establish a baseline optical phase signal. In an optional step of the inventive method, the grating structure may be treated to inhibit non-specific binding of analyte recognition material. Typically, the grating may be exposed to a surfactant, such as a dilute solution of TWEEN-20. Alternatively, a protein known not to specifically bind to the analyte recognition material may be used, such as, for example, bovine serum albumin (BSA) or the like. Alternatively, a peptide sequence may be used in connection with the present invention. Following treatment for non-specific binding, the grating may be rinsed to remove any excess surfactant, for example.

In a further step according to an embodiment of the invention, a grating having an analyte recognition material may be exposed to a sample putatively containing an analyte known to bind to the analyte recognition material disposed on the grating. The sample may be exposed to the grating under conditions that will allow binding of the analyte to the analyte recognition material. Binding conditions for specific analyte/analyte recognition materials are known in the art. Variables such as temperature, salt concentrations, pH and reaction time are known to affect binding and one of skill in the art will recognize the appropriate binding conditions for a particular analyte/analyte recognition material pair. Specific conditions are set forth in common references such as, for example, Bowtell et al., DNA Microarrays: A molecular Cloning Manual, Cold Spring Harbor Laboratory, 2002; Sambrook, Molecular Cloning: A Laboratory Manual, 3rd Edition, Cold Spring Harbor Laboratory, 2001; and Harlow et al., Using Antibodies: A Laboratory Manual: Portable Protocol No. 1, Cold Spring Harbor Laboratory, 1998, which are hereby incorporated by reference in their entirety.

A sample may be a biological sample or a chemical sample, for example. The sample may be, for example, obtained from a human or other animal or from an environmental site where the earth, water or air are to be tested. A sample may be, for example: cells, tissue, or physiological fluid, such as amniotic fluid, blood, cerebrospinal fluid, plasma, serum, saliva, semen, or other bodily fluids. A sample also may include fluid or a suspension of solids obtained from mucous membranes, wounds, tumors, or organs. Alternatively, a sample may be obtained to test for environmental contamination. For example, a surface, such as an air filter, suspected to be contaminated may be swabbed and the material obtained may be suspended in a solution for exposure to a grating. The analyte may also be contained in a gas. The analyte may be contained in air or an aerosol, for example.

Advantageously, neither the analyte nor the analyte recognition material is required to be labeled in a method according to the invention. This may permit faster processing of samples, while affording highly sensitive detection of analyte.

The exposure of the grating to the sample may be achieved in situ that is within the grating in place in the grating structure. For example, the sample may be introduced into the space between the two gratings. FIG. 6B shows such a space 130. The sample may be introduced through an inlet port 11 such as is shown in FIG. 1 and removed via the same port 11 following binding. Alternatively, the sample may be removed through an outlet port 13, such as is shown in FIG. 1.

Exposure of the grating to the sample may also be accomplished with the grating removed from the grating structure. For example, the sample may be applied to the grating, or the grating may be immersed in the sample, for the time required by the binding reaction. Subsequently, the grating may be placed in the grating structure. Optionally, the grating may be rinsed after exposure to the sample in order to remove any excess sample and to stop the binding reaction.

Following exposure of the grating to the analyte, the grating structure may be illuminated and the optical phase signal detected. Any change in the optical phase signal may be quantitated by comparison to the optical phase signal detected during the preliminary illumination step. Optionally, the amount of analyte present in the sample may be calculated using the methods described above.

EXAMPLE 1

Figure 5B:
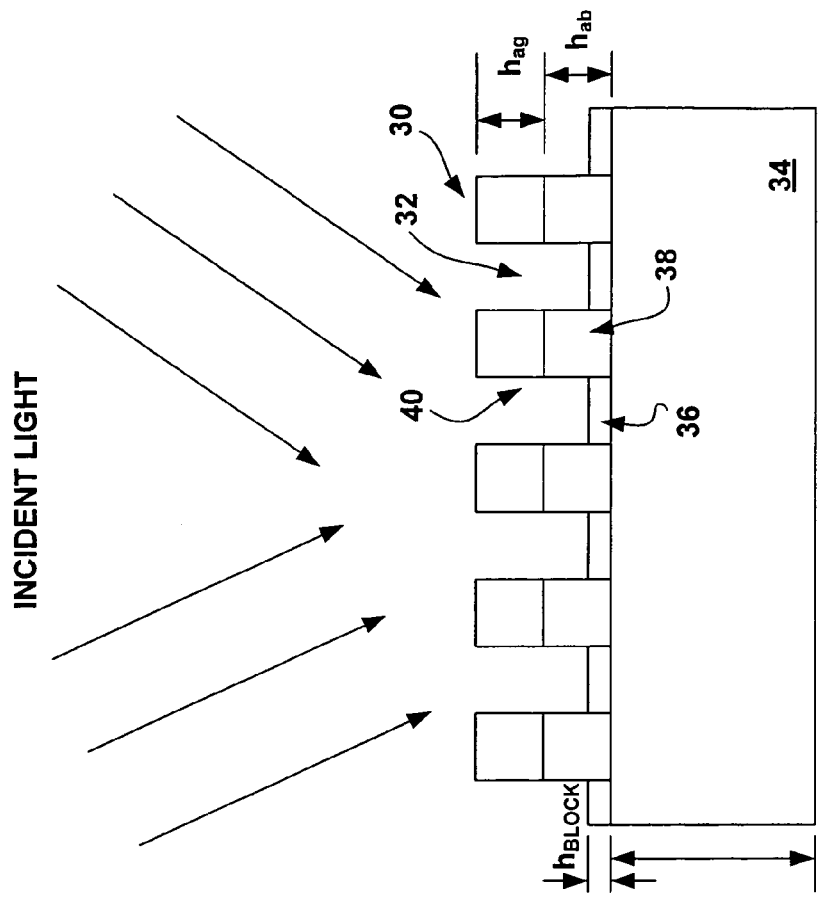
FIG. 5B shows an elevation view of a grating suitable for use in a grating sensor according to the present invention.
Figure 5A:
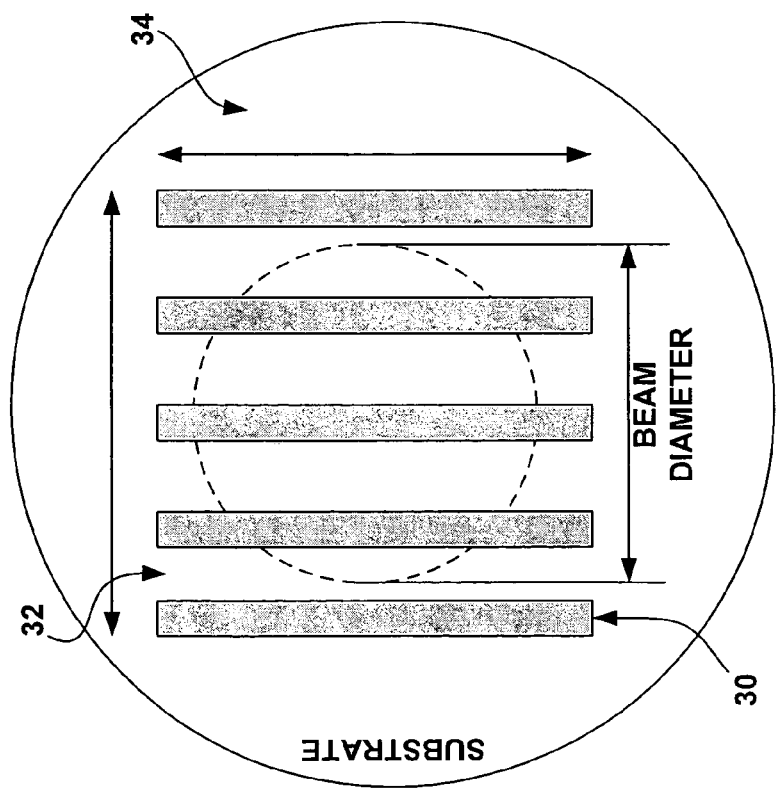
FIG. 5A shows the plan view of a grating suitable for use in a grating sensor according to the present invention.

FIG. 5A shows a plan view of a grating suitable for use in a grating sensor according to the present invention. FIG. 5B shows an elevation view of another grating suitable for use in a grating sensor according to the present invention. Molecular receptors, such as, for example, antibodies, may be placed in precise locations on the optical substrate. In this case, the antibody receptors lie in the 2 μm wide lines 30 with 2 μm wide separations 32 (a 4 μm period) and are placed on a substrate 34 made of fused silica. This 4 μm period will produce a first order diffraction angle of approximately 9 degrees at a wavelength of 633 nm. Blocking material 36 to prevent non-specific binding of receptors and analyte may be placed in the region between the lines. Upon introduction of buffer solution putatively containing the antigen corresponding to the chosen antibody, specific binding between immobilized antibody 38 and analyte 40 may occur at precise locations, e.g., at the peaks 30 of the grating. Alternatively, the binding may occur in the valleys 32 of the grating. This molecular binding may cause the physical and optical height of the grating to change. The optical height of the grating is equal to the index of refraction of the grating multiplied by the height of the grating. In this example, the heights of the antibody ($h_{ab}$) added to the height of the antigen ($h_{ag}$) layers are expected to be in the 10's of nm range. An average change in height over the illuminated region from 10 nm to 20 nm upon binding generates a sufficient signal for adequate detection. It is also expected that the incident beam would have to cover at least 2 cycles or periods in order to generate a sufficient signal.

EXAMPLE 2

FIG. 6A shows an exemplary grating sensor according to another embodiment of the present invention. The grating sensor may be configured to detect a single analyte. In FIG. 6A, the light source is a laser 50. The laser is configured to emit coherent light at a wavelength of, for example, about 633 nm. A helium-neon (He—Ne) laser may be used for this purpose. This light may be introduced into a beam splitter 52 such that two point sources are created. A commercially available single mode fiber optic coupler may be used to couple light into a single mode fiber. These two point sources may be collimated by a lens 54 and may be directed so as to be incident on the grating structure. The collimated beams may be incident upon the grating structure 56 at an angle corresponding to the +1 and −1 diffraction orders generated by the 4 µm period grating if the grating were to be illuminated at a zero degree angle of incidence with respect to the normal of the grating surface. This may produce an angle of incidence of about 9 degrees. By using a lens with, for example, a 25 mm focal length a point source separation of 7.88 mm at the output of the fiber coupler may be realized. Two gratings, such as those depicted in FIG. 5 may be used in connection with grating structure 56. The two gratings may be translated by ¼ period with respect to each other and the separation between the first grating and the second grating may be such that fluid may flow between the two gratings. The grating structure shown has a transverse dimension of ½ inch. This is adequate for optical coverage while allowing for fluid flow through the grating structure. The light passing though the grating from each incident beam is diffracted. In this configuration the +1 order of one beam is coincident and therefore interferes with the −1 diffraction order of the other beam. Both means in turn may then be coincident with the optical axis of the system. The gratings may be followed by another lens 58 which focuses the diffracted light into the far-field plane. A spatial filter 60 placed at the far-field plane eliminates the light from the unwanted orders and may be configured to allow the interference overlapped orders to pass. A collection lens 62 may be configured to direct the light onto a single detector 64. Because of the interference, the intensity of the light at the detector is indicative of the phase difference between the two diffracted beams. This phase difference in turn is indicative of the lateral translation of the grating structure which in turn is indicating of the relative heights of the two gratings which make up the grating structure. The piezoelectric transducer (PZT) may be configured to provide precise lateral movement of the grating or gratings and therefore the PZT may be a precise mechanism for introducing a known phase difference in the interfering beams. Changes in the phase caused by the binding event may show up as an electrical phase shift in the modulated signal. FIG. 6A is a ray trace using COTS (commercial off-the shelf) components and therefore, the system may be made more compact using appropriately designed components. For example, as shown in the example illustrated in FIG. 6A, the distance from the output of the fibers to the detector is approximately 6 inches.

EXAMPLE 3

FIG. 7A shows an exemplary embodiment of a grating sensor according to one aspect of the present invention. More specifically, the use of an embodiment of the present invention for detection of multiple analytes is shown in FIGS. 7A-C. The layout shown in FIGS. 7A-C may be adapted to accommodate multiple analyte detection by modifying the grating assembly to include multiple gratings, each of which may be designed to detect a different analyte. The grating structure may be placed on a stage such that each grating may be translated to pass under the probing beam of the optical system, much like a stepper in photolithography. FIG. 7A illustrates such a system.

EXAMPLE 4

FIG. 7B shows another exemplary embodiment of a grating sensor according to another embodiment of the present invention. More specifically, FIG. 7B shows a grating structure imaged onto a multi-material detector array, such as, for example, a CCD camera. The grating structure may be broadly illuminated, for example. All of the gratings are simultaneously illuminated according to this example. Each detector then may "see" only a portion of the grating structure. Judicious location of the spatial filter plane assures that the light that enters the detectors is limited to the desired interfering diffracted orders as previously described.

EXAMPLE 5

FIG. 7C shows a grating sensor including a multi-wavelength light source. The grating assembly containing multiple wavelengths may be broadly illuminated by the light from this source at a specific angle for all wavelengths. Because the diffraction angle for a given period is wavelength dependent, the period of the individual gratings is different from grating to grating. In this way, only light of a specific wavelength for each grating may be diffracted at the proper angle to pass through the spatial filter and on to the detector. At the detector, each wavelength represents the signal from one of the gratings. At this point, a spectral filter may be used to switch between the wavelengths and therefore the different gratings. Alternatively, because each grating may have a different period, each grating may generate a different signal frequency as the PZT translates the grating. Therefore, at the detector, the frequency of the signal is associated with a specific grating and therefore a specific targeted analyte while the phase of the frequency component indicates a binding event.

EXAMPLE 6

Figure 8:
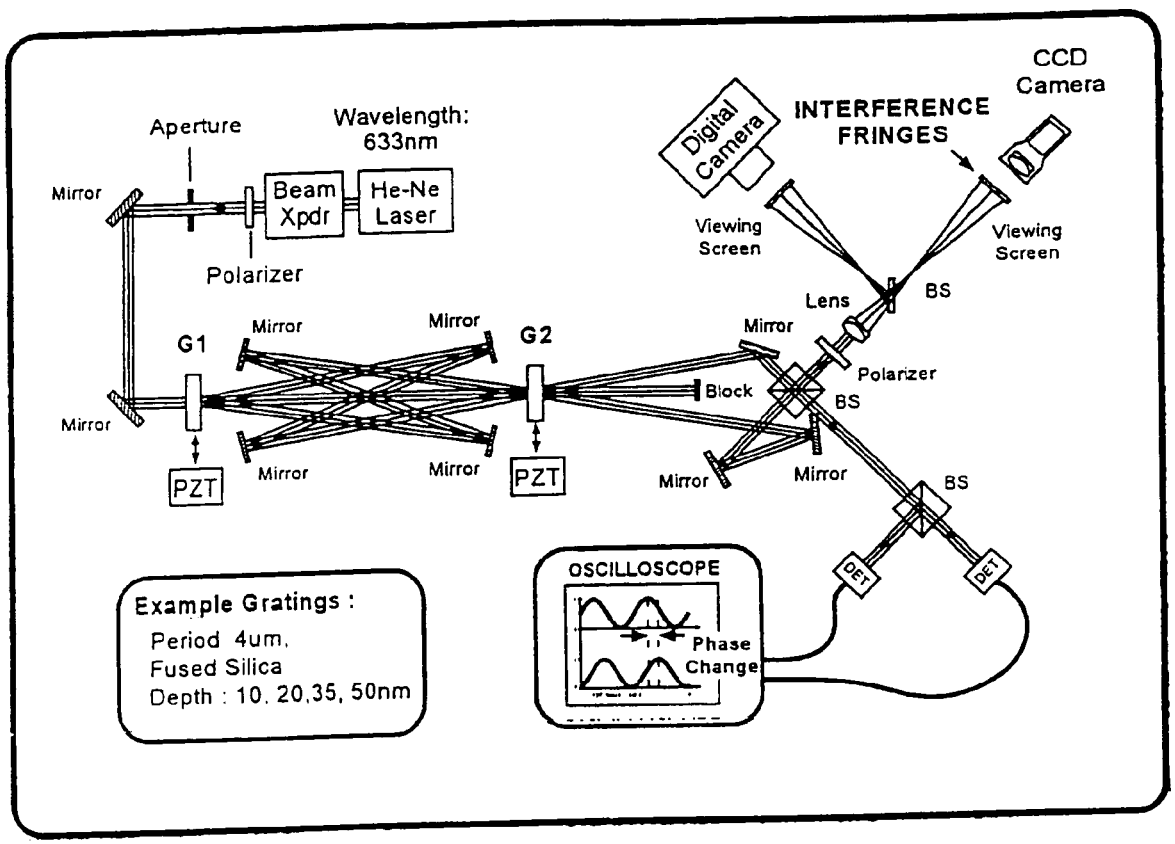
FIG. 8 shows yet another exemplary embodiment of a grating sensor according to another embodiment of the present invention.

FIG. 8 shows yet another exemplary embodiment of a grating sensor according to another embodiment of the present invention. Light from a frequency-stabilized He—Ne laser may be incident upon two separate gratings. Illumination may only be at the zero order or normal to the grating surface. The two gratings may be separated in order to gain some flexibility in alignment and in removing and inserting test gratings. The layout with the two gratings is optically equivalent to the two gratings superimposed. The diffracted light into the +1 and −1 orders for both gratings may be overlapped and made to interfere at the exit of a cube beam splitter. This configuration may be reversed from that shown in FIG. 6A. That is, in FIG. 6A, the light is incident upon the gratings in two beams at the angles corresponding to the +1 and −1 diffraction orders if the grating were illuminated at normal incidence. The resultant diffracted beams that are at an angle are collinear with the normal with respect to the grating surface may be detected. As shown in FIG. 8, the light may be incident upon the gratings in the zero order and the diffracted +1 and −1 orders are detected. The two configurations are optically equivalent. The configuration shown in FIG. 8, however, has the added benefit of ease of alignment. FIG. 8 shows three ways to view the data. A CCD camera and/or a digital camera may be configured to record the two dimensional interference pattern while the individual detectors look at a single point in the interference pattern. The second signal detector may be used as a reference. A signal detector may provide simple quantitative data with regard to the change in phase. The data from the CCD camera may also be analyzed to yield quantitative data or used to get a quick visual of the changes in the interference pattern.

EXAMPLE 7

FIG. 9 shows the results of the use of optical glass gratings without an analyte recognition material. A series of such gratings, each with a different grating modulation depth, is created in the etching process used to make fused silica gratings. The gratings may be produced to have precise modulation depths such as 10 nm, 20 nm, 35 nm, and 50 nm. Tests may be performed using two such gratings at a time to record the differences in these grating heights. These glass gratings may also serve as a reference or calibration to the set up to be compared against the signal generated by a grating containing an analyte recognition material.

Figure 9A:
FIGS. 9A-C show digital images of interferograms.
Figure 9B:
Figure 9C:
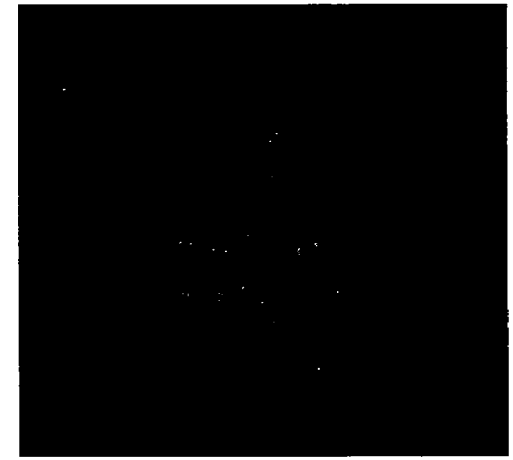

FIGS. 9A-C show digital images of interferograms. The interferograms were recorded using a digital camera, an illumination wavelength of 633 nm and optical glass gratings without an analyte recognition material disposed thereon. Tilt fringes have been introduced so as to indicate the effect of varying the depth of one of the two gratings. Adding this tilt is equivalent to adding a variable translation across the grating as a function of position. In other words, the tilt fringes assure that at some places the two gratings are displaced relative to each other by, for example, ¼ period while at other places the gratings may be exactly overlapped with no equivalent displacement. Because the shift in the optical phase as a function of grating depth is apparent when the displacement is ¼ period, the deviation of the tilt fringes is a measure of the depth ratio difference between the two gratings. The reference grating used has approximately 50 nm of etch depth. FIGS. 9A-C show the interferograms when the reference grating is paired with gratings or 0 nm, 20 nm, and 50 nm of etch depth, respectively. Note that the degree of 'slant' changes with the etch depth. This is an indication of the change in the maximum deviation of the tilt fringes and shows that at these small etch depth levels that there is a substantial change in the interferogram patterns.

Figure 10:
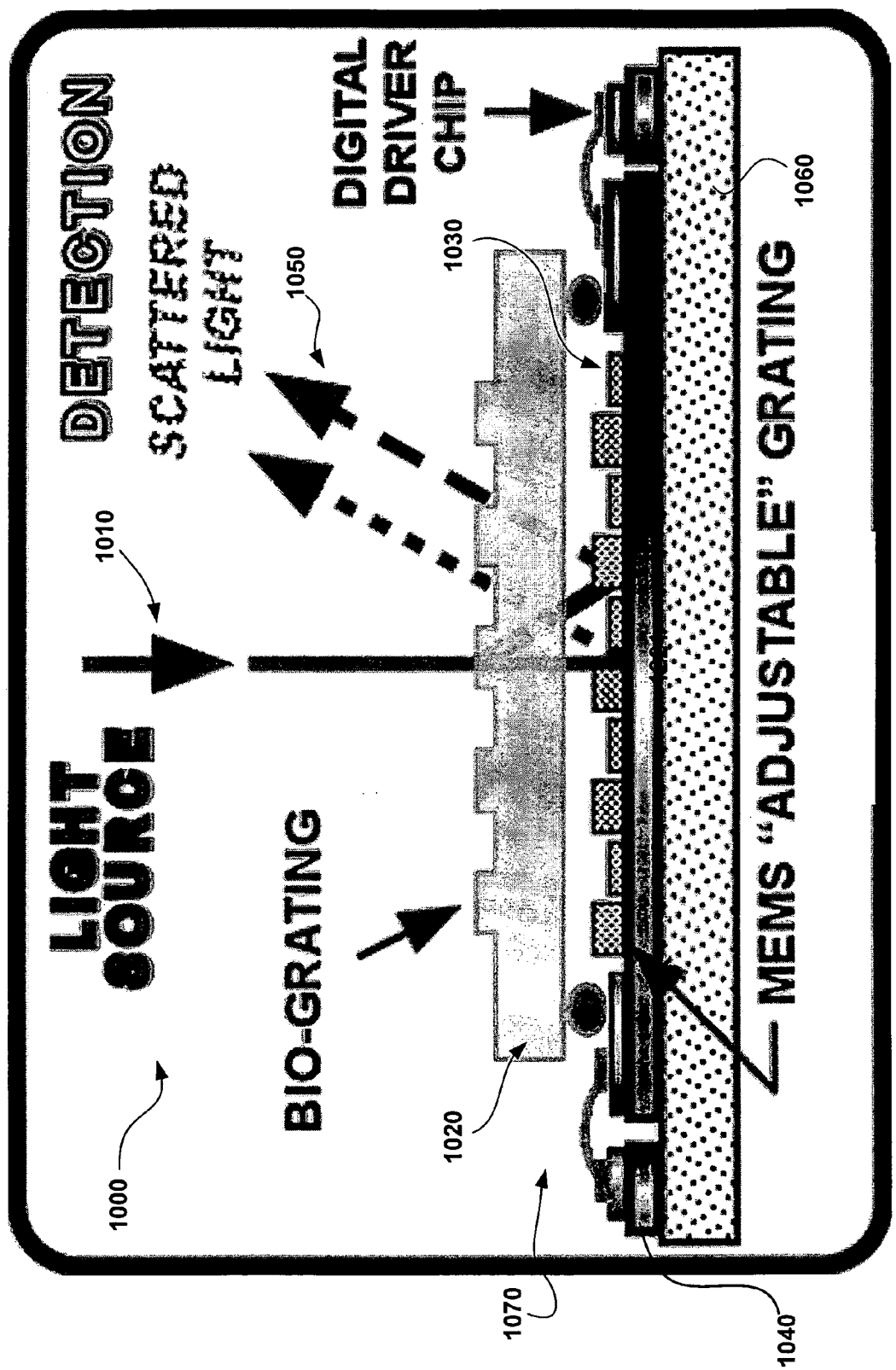
FIG. 10 shows a side profile of an exemplary embodiment of a grating sensor using a MEMS device according to an embodiment of the present invention.

FIG. 10 shows a side profile of an exemplary embodiment of a grating sensor using a MEMS device according to an embodiment of the present invention. The embodiment of the grating sensor shown in FIG. 10 may include a light source (not shown). The light source may be configured to generate light 1010. Light 1010 may be, for example, coherent light, and may be, for example, at a wavelength of 633 nm. Alternatively, the light 1010 may be light of any wavelength as long as it does not harm the analyte recognition material or otherwise detrimentally impact the sensor. Light 1010 may be incident upon a first grating 1020. As shown in FIG. 10, first grating 1010 may be, for example, a bio-grating. In other words, first grating 1020 may include an analyte recognition material disposed thereon. The analyte recognition material may be disposed on, for example, the peaks of the grating 1020. Alternatively, the analyte recognition material may be disposed in the valleys of the grating 1020. According to the embodiment of the invention illustrated in FIG. 10, the analyte recognition material may be disposed on a portion of the first grating, and the light may be transmitted through a portion of the first grating including the analyte recognition material and reflected through a portion of the grating having no analyte recognition material disposed thereon.

After light 1010 has been transmitted through the first grating 1020, it may be incident upon a micro-electrical mechanical system (MEMS) 1070 that is configured to modulate the light 1010 after it is transmitted through the first grating 1020. The MEMS may include, for example, metal or otherwise deflectable leaves 1030. These leaves 1030 may be systematically deflected using an electric or magnetic field. A driver circuit 1040 may be configured to control the MEMS 1070 so that the light 1010 is modulated at the appropriate frequency. The MEMS 1070 may be disposed on a substrate 1060. After the light is modulated by the MEMS 1070, it may be reflected back through the first grating 1020. Alternatively, the light may be reflected through a second grating (not shown). In one embodiment, the first grating and the second grating may be interconnected. The reflected light is referred to as "scattered light" 1050, and may include the diffractive orders from the grating 1020 or gratings (not shown). These orders, such as, for example, the +1 or −1 orders include the phase information, as the zero order does not contain any phase information due to the diffraction and interference of the light due to effective grating shifts.

Figure 11:
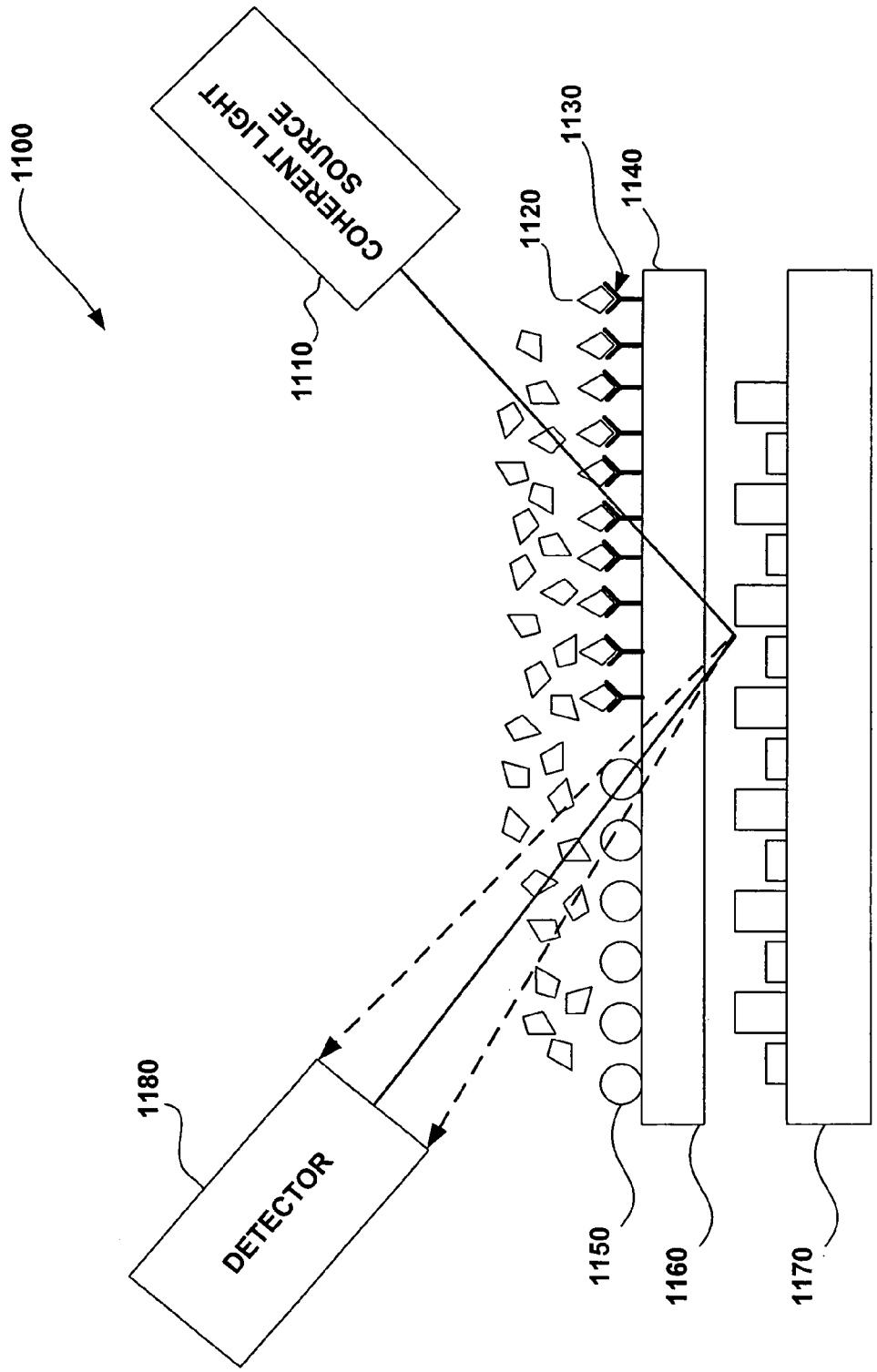
FIG. 11 shows a side profile of another exemplary embodiment of a grating sensor using a MEMS device according to another embodiment of the present invention.

FIG. 11 shows a side profile of another exemplary embodiment of a grating sensor using a MEMS device according to another embodiment of the present invention. FIG. 11 is similar to FIG. 10 in that it incorporates a MEMS to modulate the light. This is an alternative to using a PZT to physically move the gratings to thereby modulate the light as described, for example, with respect to FIG. 1. As shown in FIG. 11, a grating sensor 1100 may include a light source 1110. The light source 1110 may be, for example, a coherent light source 1110, such as, for example, a laser. According to one embodiment of the present invention, the coherent light source 1110 is a He—Ne laser that produces light at a wavelength of approximately 633 nm. It should be understood that any wavelength of visible, UV or IR light may be used in connection with the present invention after potential deleterious interactions with the analyte recognition material has been accounted for. Appropriate wavelengths based on the type of analyte recognition material being used will be apparent to those skilled in the art in light of the present disclosure.

As shown in FIG. 11, light from the light source 1110 may be incident upon a first grating section 1140. The first grating section 1140 may include an analyte recognition material 1130 disposed on the grating section 1140 in a periodic manner. The analyte recognition material 1130 may be configured to undergo binding with an analyte of interest 1120. After the light is transmitted through the first grating section 1140, it may be incident upon a MEMS 1170. The MEMS 1170 may be configured to modulate the light at a predetermined frequency. The MEMS may modulate the light at, for example, a frequency of 1 kHz, 10 kHz, or more. For example, the MEMS may modulate the signal on the order of MHz. Other modulation frequencies will be apparent to those skilled in the art based on the present disclosure. One reason for the modulation of the light is to reduce the noise effects that may be caused from various noise sources, such as, for example, acoustical vibrations, geological vibrations or other types of vibration. This may be important due to the high sensor resolution of the various sensors that may be constructed in accordance with the present invention.

After the light is modulated by the MEMS 1070, it may be directed through a second grating section 1160. The terms first grating section and second grating section are being used to reflect that the first grating section and second grating section may be part of the same grating, may be two joined gratings, or may even be two completely independent grating structures. Therefore, the term "grating section" is to be construed to cover each of these embodiments. The second grating section may have a second grating period 1050. This period may be the same as the period of the first grating section 1140. After the light is reflected through the second grating section 1160, the light may be incident upon a detector, 1180. The detector 1180 may be configured to detect a change in the phase of the light in, for example, the +1 and −1 diffractive orders. Alternatively, light in any order other than the zero order may be detected to determine a phase change in the signal that may be caused by a binding event.

Figure 12:
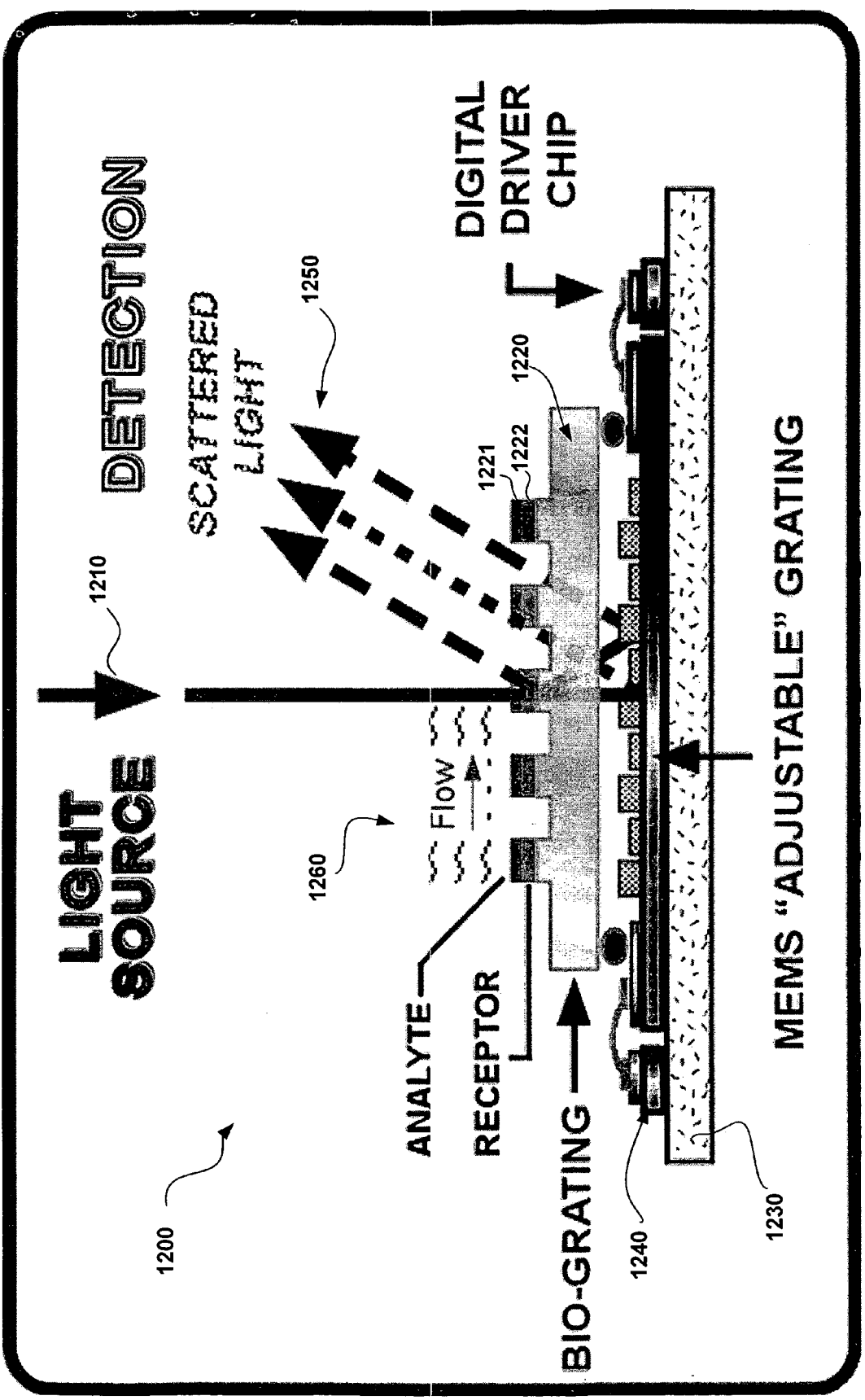
FIG. 12 shows an embodiment of a grating sensor using a MEMS device according to an embodiment of the invention.

FIG. 12 shows an embodiment of a grating sensor using a MEMS device according to an embodiment of the invention.

The solution containing the analyte is in a fluid passing over the grating 1220. This is referred to as "FLOW" in FIG. 12. According to the invention as depicted in FIG. 12, a binding event has already occurred. As shown in FIG. 12, three different beams may be diffracted by the elements in the system: a first from the grating 1220 (which is subsequently reflected off of the MEMS 1240); one from the MEMS grating 1240; and one from the grating 1220 (after the light has been reflected from the MEMS 1240).

Figure 13:
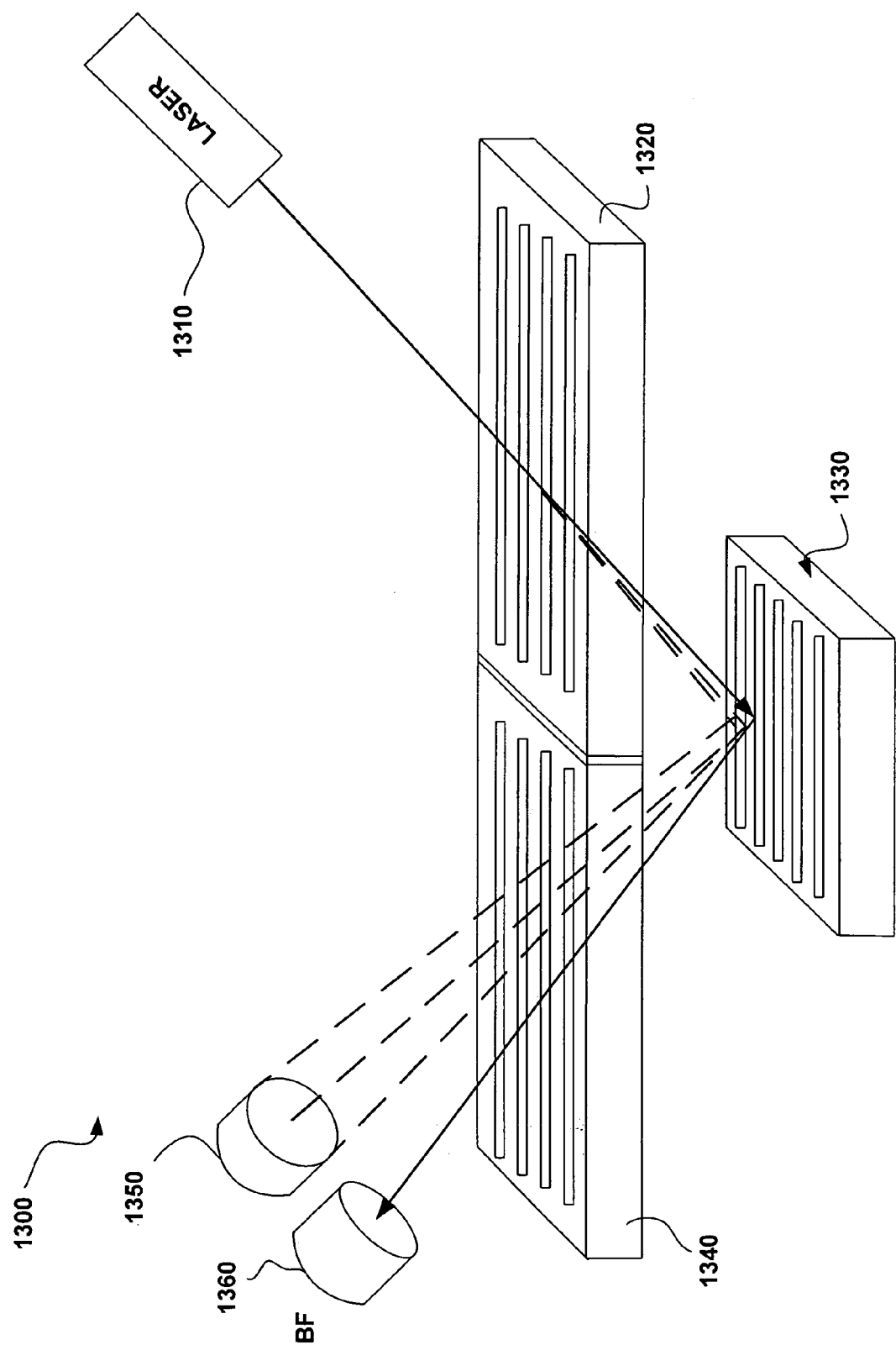
FIG. 13 shows a functional diagram of a grating sensor operating in a first mode according to an embodiment of the invention.

FIG. 13 shows an exemplary MEMS-based grating sensor according to one embodiment of the present invention. As shown in FIG. 13, light may be generated by, for example, a laser device 1310, and may be incident upon a grating section 1320. The grating section 1320 may include an analyte recognition material (not shown) disposed thereon. When the light passes through the grating section 1320, the light may be diffracted by that grating section 1320 into various diffractive orders. After the light is diffracted by the first grating 1320, it may be incident upon a MEMS 1330. The MEMS may be configured to modulate the diffracted light received from the grating 1320, and may be configured to reflect that light to, for example, a second grating section 1340. The second grating section 1340 may be the same physical grating as the first grating, but may not have an analyte recognition material disposed thereon. Alternatively, second grating section 1340 may be a different grating than the first grating 1320. The second grating section 1340 may have the same grating period and other grating properties as the first grating section 1320. The light diffracted into, for example, the +1 and −1 combined diffractive orders of gratings 1320 and 1340 may have a first phase prior to a binding event. However, after a binding event, the light diffracted into the +1 and −1 orders may have a second phase, the second phase being different than the first phase.

After the light has been diffracted and the various diffractive orders have interfered, as discussed above, the phase of the light may be detected. According to one embodiment of the present invention, a detector 1350 may be configured to detect a phase in the +1 diffractive order as discussed above. An optional bright field detector ("BF") 1360 may be used to detect the 0 order to ensure that the system is operating properly. For example, a change in the intensity in zero order may be accompanied by a change in the intensity of the light in the first order, and therefore, these two intensities may be compared to ensure that the grating sensor 1300 is operating properly. Optionally, a second detector (not shown) may be configured to detect the phase of the light in the −1 order, and this may be compared to the phase of the light in the +1 order. In theory, the relative phases in each diffractive order combination should be determinable. Therefore, the comparison of the two phase measurements from each of the +1 and −1 diffractive orders may also act as a check on the proper operation of the grating sensor 1300.

Figure 14:
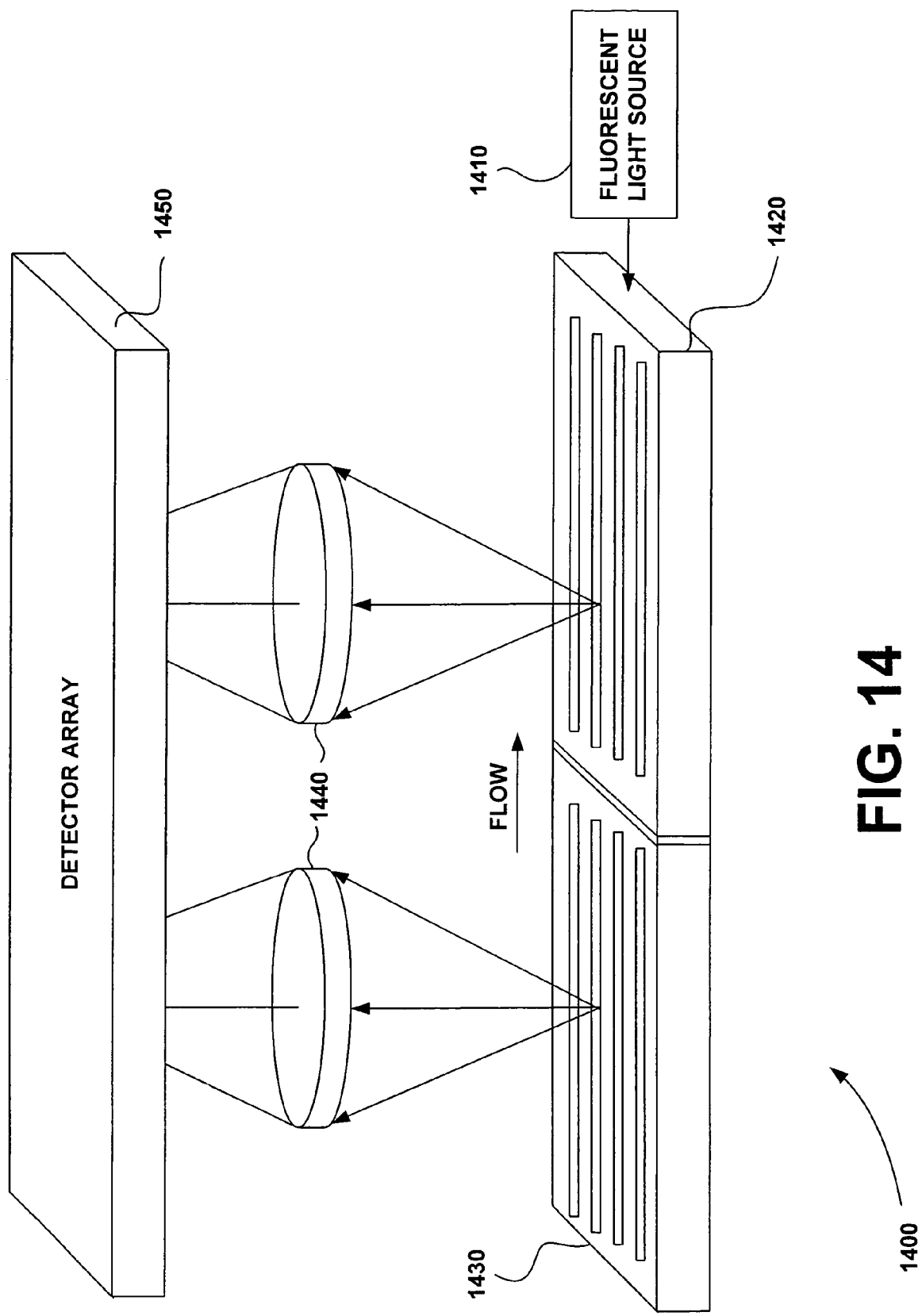
FIG. 14 shows a functional diagram of a grating sensor operating in a second mode according to an embodiment of the invention.

FIG. 14 shows a functional diagram of a grating sensor operating in a second mode according to an embodiment of the invention. According to this embodiment of the invention, the grating sensor 1400 may be configured to tag the analyte in accordance with known fluorescent tagging procedures. A light source 1410 may be used to illuminate the first grating 1420 to thereby excite fluorescence. A fluorescent tag may be a small element that is attached or bound to another structure, such as a molecule, protein or other analyte. When illuminated by a particular wavelength, the tag may become excited and release light of lower energy and hence a longer wavelength. These small elements are sometimes referred to as fluorophores or dyes. In some of the examples disclosed herein, the fluorphore may bind with an antibody. This antibody may be selected so that it may bind to a targeted analyte. After the analyte binds to the molecular receptor on the grating surface, a buffer solution containing the fluorescently tagged anyibody may be added. This solution may flow over the bound analyte. The tagged antibody may bind to the immobilized analyte. This kind of binding detection process is referred to as a sandwich assay because you have the analyte sandwiched between the untagged antibody (which attached to the surface) and the fluorescently tagged antibody. After rinsing (i.e., flow is used for flushing), light at the excitation wavelength of the tag may be used to detect the secondary binding event. When a binding event occurs for the targeted analyte, fluorescence results. This fluorescence may be imaged upon a detector array 1450 using imaging optics 1440, such as, for example, lenses.

Figure 15:
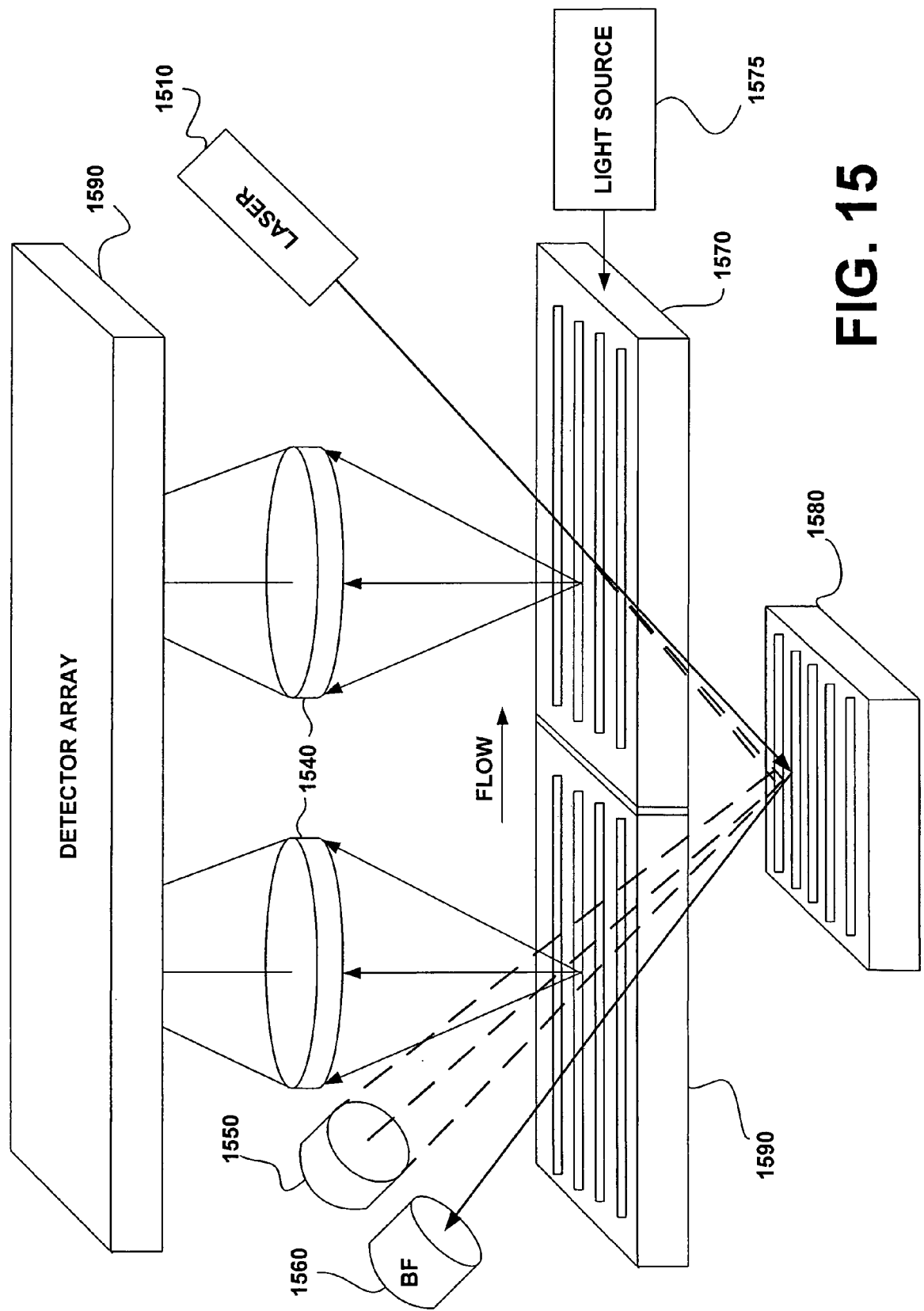
FIG. 15 shows a functional diagram of a grating sensor operating in both a first mode and a second mode according to an embodiment of the present invention.

FIG. 15 shows a functional diagram of a grating sensor operating in both a first mode and a second mode according to an embodiment of the present invention. According to the embodiment of the grating sensor 1500 (not labeled on the figure) illustrated in FIG. 15, the grating sensor 1300 illustrated in FIG. 13 may be combined with the grating sensor 1400 shown in FIG. 14. A laser 1510 may be configured to generate coherent light that is incident upon a first grating section 1570. First grating section 1520 may diffract the light received from the laser source 1510 and may be directed incident upon a MEMS 1580. The MEMS 1580 may be configured to modulate the light and may reflect the light so as to be incident upon a second grating section 1590. The phase of the light in, for example, the +1 or −1 orders may be detected. Alternatively, the phase of the light in any of the other diffractive orders, such as the +2 or −2 orders may be detected. Detector 1550 may be used to detect the phase of the light. Optional bright field detector 1560 may be used as an insurance measure to ensure that the grating sensor 1500 is operating properly, as described above. Additionally, a light source 1575 for the purpose of exciting fluorescence may be provided to illuminate the first grating 1520. By the use of a tag or label of a recognition element for the analyte, fluorescence may occur in connection with a binding event. The fluorescence may be imaged upon a detector array 1590 using imaging optics 1540.

EXAMPLE 8

Figure 16:
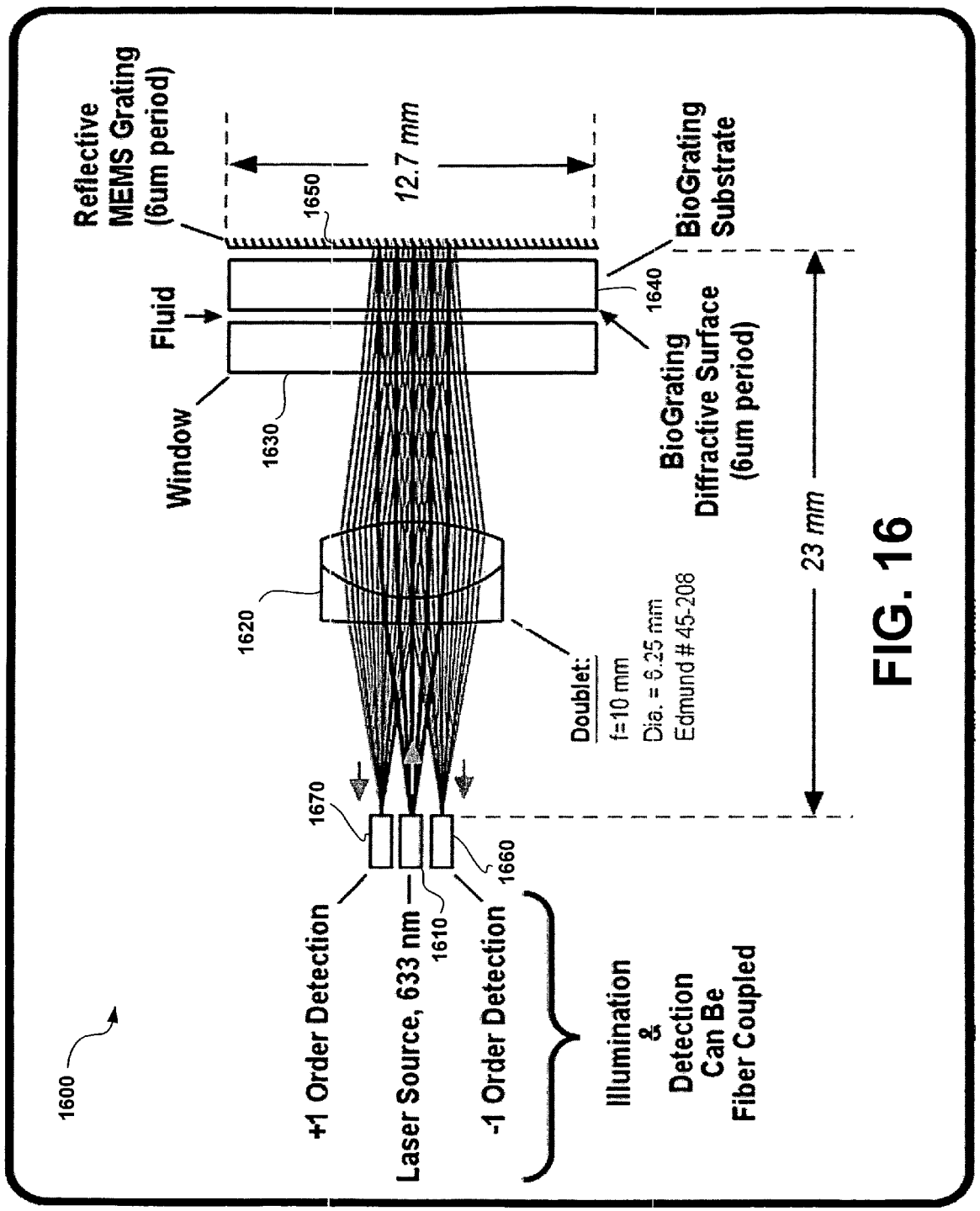
FIG. 16 shows an exemplary MEMS-based grating sensor according to one embodiment of the present invention.

FIG. 16 shows an exemplary MEMS-based grating sensor 1600 according to one embodiment of the present invention. Laser source 1610 may be configured to generate coherent light and direct the light via imaging optics 1620 to be incident upon a bio grating 1640. The bio-grating 1640 may be a grating having an analyte recognition material deposited thereon. The laser source 1610 may be, for example, a He—Ne laser source that is configured to generate light at a wavelength of approximately 633 nm. The imaging optics 1620 may include a doublet. The doublet used in accordance with this example was made by Edmund, No. 45-208 with a focal length of 10 mm and a diameter of 6.25 mm. A window 1630 may be used. The window may be included to provide a space for the fluid. It is part of the apparatus, which contains the fluids and provides a transparent port for the light to pass through. The period of the bio-grating was 6 microns, and the grating had a width of 12.7 mm. A reflective MEMS 1650 having a period of 6 microns was used to modulate the light and reflect it back through the optical grating sensor 1600. The optical phase associated with the light in the +1 and −1 diffractive orders may be detected using optical detectors 1660 and 1670. The length of the MEMS-based grating sensor 1600 may be approximately 23 mm. The period of the bio-gratings and the MEMS are, of course, exemplary and are not to be considered as limiting the implementation of the present invention.

EXAMPLE 9

Figure 17:
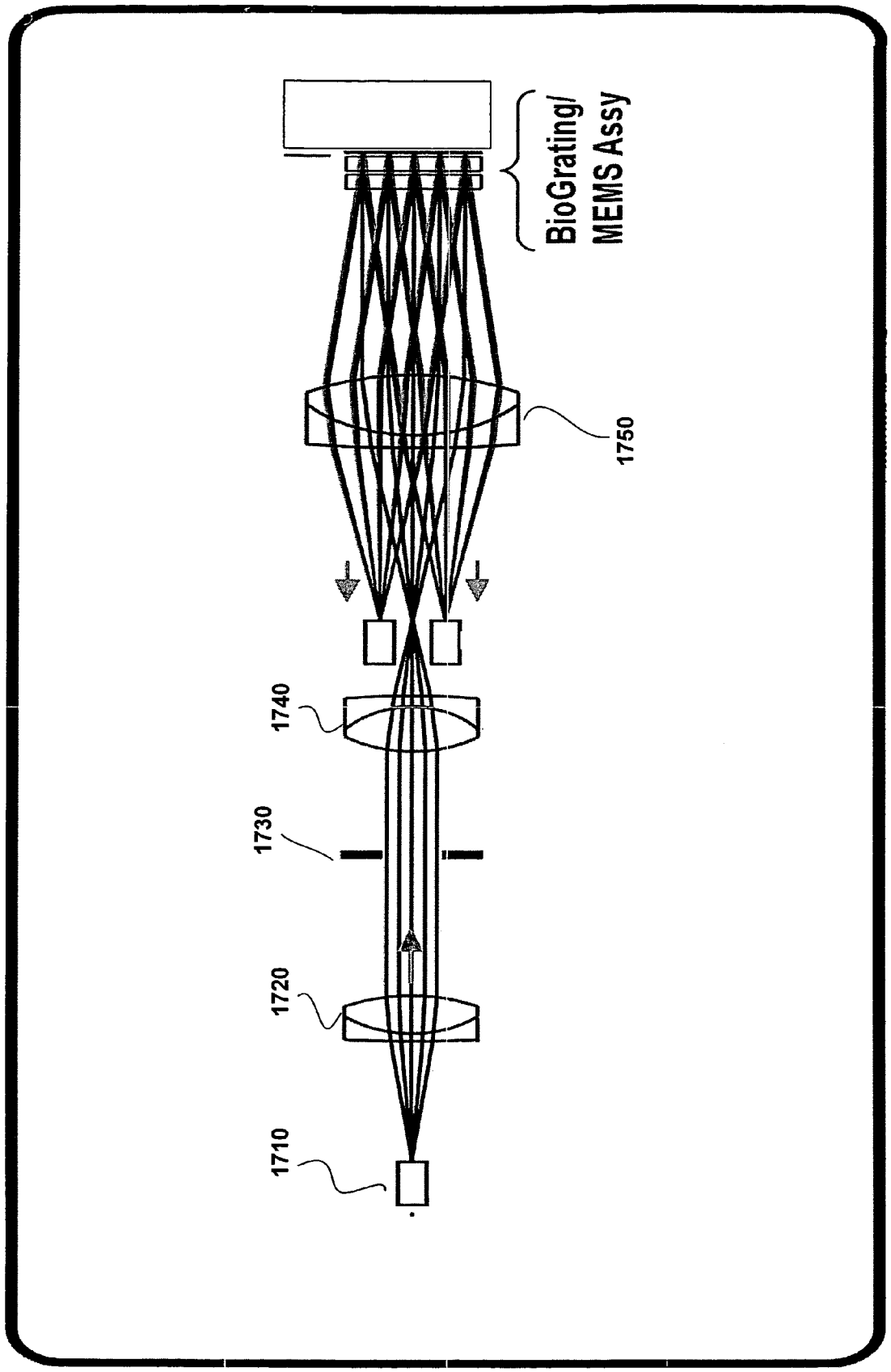
FIG. 17 shows another exemplary MEMS-based grating sensor according to a second embodiment of the present invention.

FIG. 17 shows another exemplary MEMS-based grating sensor according to a second embodiment of the present invention. A laser source 1710 may be configured to generate light and direct the light so as to be incident upon imaging optics 1720, 1730, 1740. The laser 1710 may be, for example, a He—Ne laser source 1710, configured to generate light at approximately 633 nm. The imaging optics may include a first doublet 1720, an aperture stop 1730, and a second doublet 1740. The first doublet 1720 may be, for example, an Edmund 32-309 lens with a focal length of 20 mm and a diameter of 12.5 mm. The second doublet 1740 may be an Edmund 45-209having a focal length of 14 mm and a diameter of 12.5 mm. These optics may be configured to direct the light from laser 1710 to a third doublet 1750. The third doublet 1750 may be an Edmund 45-175 lens, having a focal length of about 30 mm and a diameter of 20 mm. The third doublet 1750 may be configured to direct light so as to be incident upon a window 1760 and a grating 1770 having an analyte recognition material deposited thereon. The light may be transmitted through window 1760 and bio-grating 1770 to be incident upon MEMS 1780. The MEMS 1780 may be configured to modulate the light and reflect it back through the optical grating sensor 1700. A first detector 1790 and a second detector 1795 may be configured to detect a phase shift of the light caused by a binding event. In this example, the length of the optical system was 146 mm. Thus, the grating sensor 1700 of the present invention may be compact. The aperture stop may be added to permit control of the beam size and shape at the grating location. The grating location may be selected to be at a conjugate (i.e. pupil) location. By doing so, the beam can be optimally matched to the grating geometry thereby enhancing signals and eliminating noise.

EXAMPLE 10

Figure 18:
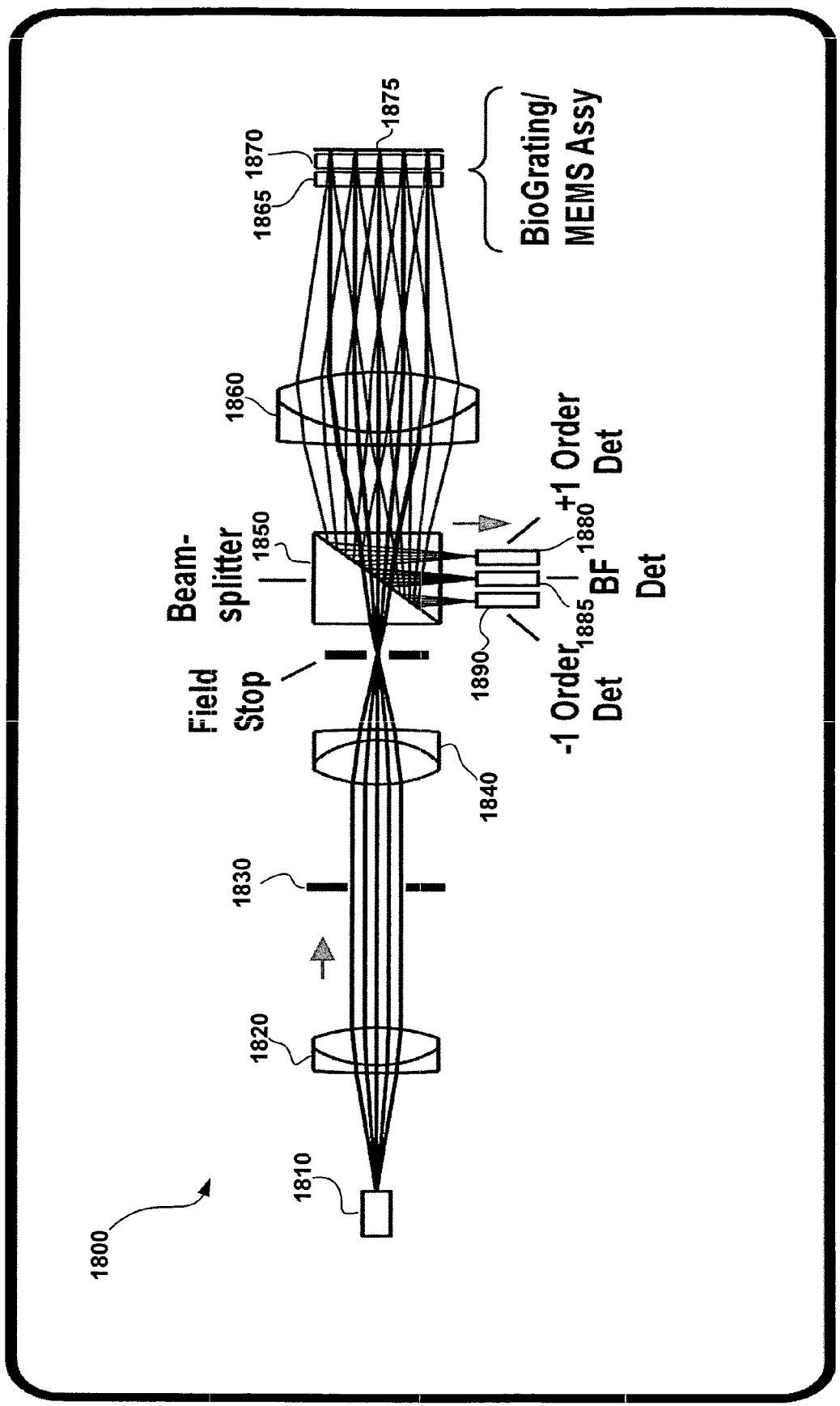
FIG. 18 shows yet another exemplary MEMS-based grating sensor according to another embodiment of the present invention.

FIG. 18 shows yet another exemplary MEMS-based grating sensor 1800 according to another embodiment of the present invention. This example may be configured to use similar optics as the example show in FIG. 17. For example, the grating sensor 1800 may be configured to use a He—Ne laser source 1810, a first doublet 1820, an aperture stop 1830, a second doublet 1840, and a third doublet 1860. This exemplary implementation of the present invention may also use a field stop, which maybe located at the focal point of the second doublet 1840. The third doublet 1860 may direct the light to be incident upon a window 1865. After the light passes through the window, it may be directed upon a grating 1870. The grating 1870 may include an analyte recognition material and may be configured to transmit the light received from the window 1865 to a MEMS 1875. The MEMS 1875 may be configured to modulate the light received and reflect it back though the optical grating sensor 1800. The light may be incident upon a beam splitter 1850 and may be configured to direct the light upon a series of detectors, 1880, 1885, 1890. The detectors may include a detector for detecting the phase of the light associated with the +1 diffractive order 1880, a detector for detecting the bright field or the zero order 1885, and a detector for detecting the phase of the light associated with the −1 order 1895. These detectors 1880, 1885, 1890 may be configured to provide signals to act as a status check to ensure that the grating sensor 1800 is operating properly, as discussed above. In this example, the beamsplitter may be added to gain access ot the field stop location independent of the plane which contains the detectors. Access to this field stop on the illumination path towards the gratings may be important to thereby reduce background light (i.e., a noise source). An aperture placed at the field stop filters the angular spread of the light incident upon the grating. This can help clean up the light source.

EXAMPLE 11

Figure 19:
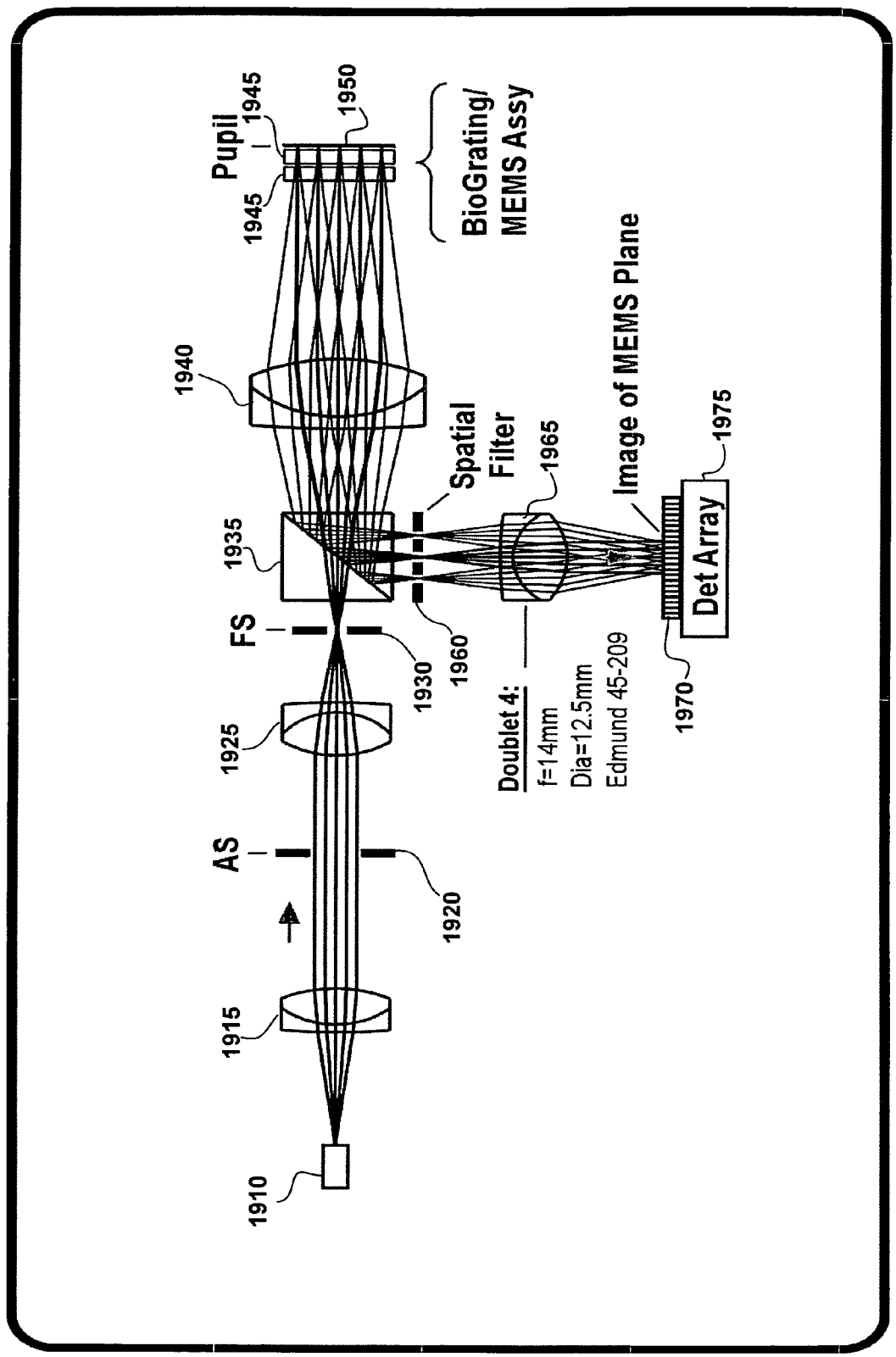
FIG. 19 shows another exemplary MEMS-based grating sensor according to another embodiment of the present invention.

FIG. 19 shows another exemplary MEMS-based grating sensor according to another embodiment of the present invention. As discussed with respect to Example 9, a grating sensor according to an eleventh example of an implementation of the present invention may include a laser source 1910, such as, for example, a He—Ne laser source, a first doublet 1915, an aperture stop 1920, a second doublet 1925, a field stop 1930, a beam splitter 1935, and a third doublet 1940. The light may be generated by the laser source 1910 and directed upon the first doublet 1915, which may collimate the light. An aperture stop 1920 may be used to clean up and shape the beam and the beam may be directed upon a second doublet 1925. The light may be directed through a field stop 1930, which may be located at the focal point of the second doublet 1925. The light may be directed to a beam splitter 1935 and to the third doublet 1940. The light may be incident upon a window 1945 and may be transmitted to a grating 1950. After the light passes through the grating, it may be incident upon a MEMS device 1955, which may be configured to modulate the light and reflect it back through the optical grating sensor 1900. The reflected light may be directed through a spatial filter 1965 and may be passed through a fourth doublet 1965 to be incident upon a detector array 1975. The fourth doublet 1965 may be an Edmund 45-209 doublet having a diameter or 12.5 mm and a focal length of 14 mm. The fourth doublet 1965 may be configured to form an image of the MEMS plane 1970 upon the detector array. In this example, there is the additional access to the field plane on the return path of the light from the grating. At this plane and aperture or spatial filter can be added to select the light that enters the detector array. This location for the spatial filter is equivalent to selecting the desired angular spread of light from the grating. This spatial filtering could also be dynamic allowing the selected orders to pass through as a function of time. In this way, the zero order and the +/−1 orders may be periodically measured as desired.

While specific embodiments of the present invention have been described, numerous other embodiments and components may be used in connection with an optical grating sensor according to the present invention. For example, specific embodiments of the present invention were described as detecting a single analyte. Numerous other constructions of the present invention are possible where multiple analytes may be detected using multiple analyte recognition materials. Additionally, while the laser source described was a He—Ne laser, and the wavelength of the light was described as being about 633 nm, any type of a laser may be used as long as the wavelength of the light does not harm the analyte or analyte recognition material. For example, a frequency doubled YAG laser may be used in accordance with the present invention.

Additionally, polarization-maintaining components may be employed to ensure that the polarization of the light is maintained or otherwise controlled to ensure that a maximum amount of interference between the diffracted orders of the light is obtained at the image plane (i.e., the detector or detectors).

Numerous other configurations of an optical grating sensor may be implemented based on the present disclosure. While the invention has been described with reference to specific preferred embodiments, it is not limited to these embodiments. For example, while certain embodiments of the invention were described with respect to tagging and fluorescence, various other tagging or labeling systems may be used. For example, the label may be a luminescent label, a phosphorescent label, an up-converting label, a down-converting label, a bead-based label, or a metal-colloid label. These other methods of labeling are known in the art. The invention may be modified or varied in many ways and such modifications and variations as would be obvious to one of skill in the art are within the scope and spirit of the invention and are included within the scope of the following claims.

What is claimed is:

1. An apparatus comprising: a coherent light source; a first diffraction grating, the first diffraction grating having a first period; a micro-electrical mechanical system (MEMS), the MEMS being displaced from the first diffraction grating and being configured to modulate and induce a phase shift in light received from the coherent light source; an analyte recognition material disposed on the surface of the first diffraction grating; and a detector configured to receive light from the coherent light source after the light has been diffracted from the first diffraction grating and modulated by the MEMS.

2. The apparatus of claim 1, wherein the MEMS is configured to simulate a lateral displacement of a grating with respect to a normal of the first grating.

3. The apparatus of claim 2, wherein the lateral displacement is a displacement of less than one period.

4. The apparatus of claim 3, wherein the lateral displacement is a displacement of approximately {fraction (¼)} period.

5. The apparatus of claim 1, further comprising: a spatial filter disposed relative to the MEMS such that predetermined orders of diffracted light are prevented from reaching the detector.

6. The apparatus of claim 1, wherein the MEMS is configured to modulate the light at a frequency of approximately 1 kHz or more.

7. The apparatus of claim 1, wherein the MEMS is configured to modulate the light at a frequency of approximately 10 kHz or more.

8. The apparatus of claim 1, wherein the analyte recognition material is one of an antibody, antigen, peptide, nucleic acid, cell, phage display, protein, lectin, molecular imprinted polymer (MIP), fellerene, carbon nanotube, and a carbon-based nano-system.

9. The apparatus of claim 1, the detector being a first detector, the apparatus further comprising: a light source, the light source being configured to excite a fluorescent marker thereby causing spontaneous emission from the fluorescent marker; a second detector, the second detector being configured to receive energy from the spontaneous emission.

10. A method for examining light, comprising: illuminating a first grating with light from a coherent light source, the first grating including an analyte recognition material deposited thereon; receiving the light from the coherent light source at a micro-electrical mechanical system (MEMS) after the light passes through the grating including the analyte recognition material; modulating the light received at the MEMS at a frequency; and detecting a phase of the light received from the MEMS at a detector.

11. The method of claim 10, wherein the MEMS is configured to modulate the light at a frequency of approximately 1 kHz or more.

12. The method of claim 10, wherein the MEMS is configured to modulate the light at a frequency of approximately 10 kHz or more.

13. The method of claim 10, wherein the MEMS is configured to simulate a lateral displacement of a grating with respect to the first grating.

14. The method of claim 13, wherein the lateral displacement is approximately (¼) period.

15. The method of claim 10, wherein detecting a phase of the light received from the MEMS at a detector includes detecting a phase change of the light due to a binding event.

* * * * *